(12) United States Patent
Lukenbach et al.

(10) Patent No.: US 6,489,286 B1
(45) Date of Patent: *Dec. 3, 2002

(54) PERSONAL CLEANSING COMPOSITIONS

(75) Inventors: Elvin R. Lukenbach, Flemington, NJ (US); Victoria F. Dole, Whitehouse Station, NJ (US); Glenn A. Nystrand, Lebanon, NJ (US); Laura McCulloch, Basking Ridge, NJ (US); William D. Allan, Worthing (GB); Jonathan R. Hill, Lenton (GB); Charles J. Taylor, Emsworth (GB)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/487,109

(22) Filed: Jan. 19, 2000

Related U.S. Application Data

(62) Division of application No. 08/789,593, filed on Jan. 24, 1997, now Pat. No. 6,090,773.
(60) Provisional application No. 60/010,784, filed on Jan. 29, 1996.

(30) Foreign Application Priority Data

Jan. 3, 1997 (GB) .............................................. 9700059

(51) Int. Cl.$^7$ .............................. C11D 9/00; C11D 15/00
(52) U.S. Cl. ....................... 510/475; 510/119; 510/120; 510/123; 510/124; 510/125; 510/127; 510/466; 510/477; 510/479
(58) Field of Search ................................ 510/475, 119, 510/120, 123, 124, 125, 127, 466, 477, 479

(56) References Cited

U.S. PATENT DOCUMENTS

| | | |
|---|---|---|
| 2,826,551 A | 3/1958 | Geen |
| 3,932,610 A | 1/1976 | Rudy et al. |
| 3,950,510 A | 4/1976 | Adams |
| 3,964,500 A | 6/1976 | Drakoff |
| 3,966,649 A | 6/1976 | Cheng |
| 3,980,769 A | 9/1976 | Ghilardi et al. |
| 4,075,131 A | 2/1978 | Sterling .................. 252/542 |
| 4,215,064 A | 7/1980 | Lindemann et al. ........ 260/403 |
| 4,220,548 A | 9/1980 | Hashimoto et al. |
| 4,233,192 A | 11/1980 | Lindemann et al. ........ 252/545 |
| RE30,641 E | 6/1981 | Verdicchio et al. ......... 252/526 |
| 4,292,212 A | 9/1981 | Melby |
| 4,298,494 A | 11/1981 | Parslow et al. |
| 4,337,166 A | 6/1982 | Hill et al. |
| 4,364,837 A | 12/1982 | Pader |
| 4,371,517 A | 2/1983 | Vanlerberghe et al. |
| 4,372,869 A | 2/1983 | Lindemann et al. ........ 252/174 |
| 4,380,637 A | 4/1983 | Lindemann et al. ........ 548/112 |
| 4,382,036 A | 5/1983 | Lindemann et al. ........ 260/403 |
| 4,420,410 A | 12/1983 | Huttinger .................. 252/117 |
| 4,435,300 A | 3/1984 | Guth et al. ................ 252/117 |
| 4,452,732 A | 6/1984 | Bolich, Jr. |
| 4,507,280 A | 3/1985 | Pohl et al. ................. 424/70 |
| 4,534,877 A | 8/1985 | Russell et al. .............. 252/106 |
| 4,559,227 A | 12/1985 | Chandra et al. |
| 4,567,038 A | 1/1986 | Ciaudelli et al. ............. 424/59 |
| 4,586,518 A | 5/1986 | Cornwall et al. |
| 4,591,610 A | 5/1986 | Grollier |
| 4,601,902 A | 7/1986 | Fridd et al. |
| 4,617,414 A | 10/1986 | Lukenbach et al. ........... 588/87 |
| 4,636,329 A | 1/1987 | Steuri ....................... 252/106 |
| 4,656,043 A | 4/1987 | Hawkins et al. |

(List continued on next page.)

FOREIGN PATENT DOCUMENTS

| | | |
|---|---|---|
| AR | 230181 | 3/1984 |
| AR | 230565 | 5/1984 |
| AR | 235053 | 5/1987 |
| AU | 591543 | 12/1989 |
| AU | 620746 | 6/1991 |
| AU | 619545 | 1/1992 |
| AU | 639351 | 1/1992 |
| AU | 639810 | 1/1992 |
| AU | 624514 | 6/1992 |
| AU | 653216 | 11/1992 |
| AU | 92-18636 | 1/1993 |
| AU | 651236 | 2/1993 |
| AU | 660537 | 9/1993 |
| AU | 35503/93 | 10/1993 |
| AU | 643517 | 11/1993 |
| AU | 630535 | 6/1994 |
| AU | 651972 | 8/1994 |
| AU | 652257 | 8/1994 |
| AU | 674255 | 5/1995 |
| CA | 1265748 | 2/1990 |
| CA | 1275253 | 10/1990 |
| CA | 2017672 | 11/1990 |
| CA | 2031382 | 6/1991 |
| CA | 1295949 | 2/1992 |
| CA | 2097836 | 6/1992 |
| CA | 2066885 | 10/1992 |
| CA | 2092779 | 9/1993 |
| CN | 92113769.9 | 6/1993 |
| CN | 93118593 | 6/1994 |
| CN | 94116881.6 | 6/1995 |
| DE | 0 080 977 | 6/1983 |
| DE | 0 681 832 A2 | 11/1996 |
| EP | 0 024 031 | 2/1981 |

(List continued on next page.)

OTHER PUBLICATIONS

Plate, Holger, "Alkylpolyamphocaroxyglycinates –a new class of true amphoterics," Paper presented at the International Conference on Cosmetology, Nov. 1995 in Karlovy Vary, Czech Republic, pp. 1–6 and Figs. 1–20.

Primary Examiner—Margaret Medley
(74) Attorney, Agent, or Firm—Erin M. Harriman

(57) ABSTRACT

A conditioning shampoo composition comprised of a mixture of anionic and amphoteric surfactants and optional conditioners which imparts cleansing, wet detangling, dry detangling and manageability to hair and which is relatively non-irritating and thus suitable for use by young children and adults having sensitive skin and eyes.

73 Claims, No Drawings

U.S. PATENT DOCUMENTS

| | | | |
|---|---|---|---|
| 4,663,158 A | 5/1987 | Wolfram et al. ............... 424/70 |
| 4,676,978 A | 6/1987 | Cseh | |
| 4,704,272 A | 11/1987 | Oh et al. | |
| 4,710,374 A | 12/1987 | Grollier et al. | |
| 4,741,855 A | 5/1988 | Grote et al. | |
| 4,752,467 A | 6/1988 | Konrad et al. ................ 424/70 |
| 4,769,169 A | 9/1988 | Fishlock-Lomax .......... 252/106 |
| 4,788,006 A | 11/1988 | Bolich, Jr. et al. | |
| 4,839,166 A | 6/1989 | Grollier et al. | |
| 4,842,849 A | 6/1989 | Grollier et al. | |
| 4,898,725 A | 2/1990 | Hoeffkes et al. | |
| 4,946,136 A | 8/1990 | Fishlock-Lomax .......... 252/546 |
| 4,954,335 A | 9/1990 | Janchipraponveg et al. .. 424/70 |
| 4,963,535 A | 10/1990 | Sebag et al. .................. 514/54 |
| 4,971,786 A | 11/1990 | Grollier et al. | |
| 4,996,059 A | 2/1991 | Grollier et al. | |
| 4,997,641 A | 3/1991 | Hartnett et al. ............... 424/70 |
| 5,002,762 A | 3/1991 | Bolich, Jr. .................. 424/70 |
| 5,009,880 A | 4/1991 | Grollier et al. | |
| 5,034,218 A | 7/1991 | Duvel | |
| 5,037,818 A | 8/1991 | Sime | |
| 5,051,250 A | 9/1991 | Patel et al. .................... 424/70 |
| 5,077,041 A | 12/1991 | Yamashina et al. | |
| 5,085,857 A | 2/1992 | Reid et al. | |
| 5,089,252 A | 2/1992 | Grollier et al. | |
| 5,104,642 A | 4/1992 | Wells et al. | |
| 5,120,531 A | 6/1992 | Wells et al. | |
| 5,120,532 A | 6/1992 | Wells et al. | |
| 5,137,715 A | 8/1992 | Hoshowski et al. | |
| 5,139,772 A | 8/1992 | Morita et al. ............... 424/7.06 |
| 5,145,607 A | 9/1992 | Rich .......................... 252/547 |
| 5,148,822 A | 9/1992 | Akhtar ........................ 424/70 |
| 5,151,210 A | 9/1992 | Steuri et al. | |
| 5,152,914 A | 10/1992 | Forster et al. | |
| 5,180,584 A | 1/1993 | Sebag et al. | |
| 5,186,928 A | 2/1993 | Birtwistle | |
| 5,188,756 A | 2/1993 | Baker et al. | |
| 5,194,250 A | 3/1993 | Grollier et al. | |
| 5,211,941 A | 5/1993 | Komori et al. ............... 424/70 |
| 5,213,716 A | 5/1993 | Patel et al. | |
| 5,221,530 A | 6/1993 | Janchitrapronveg et al. .. 424/70 |
| 5,225,112 A * | 7/1993 | Miyazawa et al. .......... 252/545 |
| 5,246,694 A | 9/1993 | Birthwistle | |
| 5,248,445 A | 9/1993 | Rizvi et al. | |
| 5,254,336 A | 10/1993 | Hoshowski et al. .......... 424/70 |
| 5,275,761 A | 1/1994 | Bergmann .................. 252/551 |
| RE34,584 E | 4/1994 | Grote et al. | |
| 5,302,322 A | 4/1994 | Birtwistle | |
| 5,306,489 A | 4/1994 | Goldberg et al. ............. 424/71 |
| 5,358,667 A | 10/1994 | Bergmann .................. 252/547 |
| 5,389,279 A | 2/1995 | Au et al. | |
| 5,389,364 A | 2/1995 | Cifuentes et al. | |
| 5,391,368 A | 2/1995 | Gerstein | |
| 5,393,519 A | 2/1995 | Dowell et al. ............ 424/70.11 |
| 5,409,628 A | 4/1995 | Heinz et al. | |
| 5,417,965 A | 5/1995 | Janchiprapoveg et al. ....................... 424/70.12 |
| 5,439,682 A | 8/1995 | Wivell et al. ................ 724/401 |
| 5,456,863 A | 10/1995 | Bergmann | |
| 5,478,490 A | 12/1995 | Russo et al. | |
| 5,534,248 A | 7/1996 | Matsuo et al. | |
| 5,540,853 A | 7/1996 | Trenk et al. ................. 510/152 |
| 5,543,074 A | 8/1996 | Hague et al. | |
| 5,573,709 A | 11/1996 | Wells | |
| 5,599,549 A | 2/1997 | Wivell et al. ............... 424/70.1 |
| 5,612,301 A | 3/1997 | Inman | |
| 5,614,180 A | 3/1997 | Chung | |
| 6,090,773 A * | 7/2000 | Lukenbach et al. .......... 510/475 |

FOREIGN PATENT DOCUMENTS

| | | |
|---|---|---|
| EP | 0 067 635 | 12/1982 |
| EP | 067635 | 12/1982 |
| EP | 0 074 264 | 3/1983 |
| EP | 0 102 736 | 3/1984 |
| EP | 0 127 580 | 5/1984 |
| EP | 0 112 046 | 6/1984 |
| EP | 127580 | 12/1984 |
| EP | 0 141 593 | 5/1985 |
| EP | 160507 | 11/1985 |
| EP | 0 186 453 | 7/1986 |
| EP | 0 193 386 | 9/1986 |
| EP | 0 194 097 | 9/1986 |
| EP | 0 277 876 | 1/1988 |
| EP | 0 257 807 B1 | 3/1988 |
| EP | 0 269 107 | 6/1988 |
| EP | 162600 | 9/1988 |
| EP | 0 308 189 | 3/1989 |
| EP | 0 308 190 | 3/1989 |
| EP | 0 337 354 B1 | 10/1989 |
| EP | 0 347 199 B1 | 12/1989 |
| EP | 0 358 216 B1 | 3/1990 |
| EP | 0 401 567 | 12/1990 |
| EP | 0 401 867 | 12/1990 |
| EP | 0 018 717 | 1/1991 |
| EP | 0 409 005 | 1/1991 |
| EP | 0416447 | 3/1991 |
| EP | 0 416 447 | 3/1991 |
| EP | 426906 | 5/1991 |
| EP | 432951 | 6/1991 |
| EP | 0 453 238 A1 | 10/1991 |
| EP | 0463780 | 1/1992 |
| EP | 0 463 780 | 1/1992 |
| EP | 468721 | 1/1992 |
| EP | 0 503 507 | 9/1992 |
| EP | 0 524 434 | 1/1993 |
| EP | 0 529 883 | 3/1993 |
| EP | 0 532 272 A2 | 3/1993 |
| EP | 0560519 | 5/1993 |
| EP | 0 552 024 | 7/1993 |
| EP | 0 562 638 A2 | 9/1993 |
| EP | 0 565 753 | 10/1993 |
| EP | 0 567 326 | 10/1993 |
| EP | 569028 | 11/1993 |
| EP | 578747 | 1/1994 |
| EP | 0 627 217 A2 | 4/1994 |
| EP | 595493 | 5/1994 |
| EP | 0 571 543 | 3/1995 |
| EP | 0 642 782 | 3/1995 |
| EP | 0 670 158 A2 | 9/1995 |
| EP | 0 511 652 B1 | 11/1995 |
| EP | 0 548 265 | 12/1995 |
| FR | 0 603 078 A1 | 6/1994 |
| FR | 0 662 315 A1 | 7/1995 |
| GB | 1 437 912 | 6/1976 |
| GB | 1 443 959 | 7/1976 |
| GB | 1 470 234 | 4/1977 |
| GB | 2 039 938 | 8/1980 |
| GB | 1 584 127 | 2/1981 |
| GB | 1 584 364 | 2/1981 |
| GB | 1 603 321 | 11/1981 |
| GB | 2 114 995 | 9/1983 |
| GB | 2 122 214 B | 1/1984 |
| GB | 2 122 898 B | 1/1984 |
| GB | 2 135 332 B | 8/1984 |
| GB | 2 245 585 | 1/1992 |
| GB | 2 246 363 | 1/1992 |
| GB | 2 255 101 B | 10/1992 |
| GB | 2246708 A * | 12/1992 |
| GB | 2283755 | 5/1995 |
| IT | 1051257 | 4/1981 |

| | | | | | | |
|---|---|---|---|---|---|---|
| IT | 1083535 | 5/1985 | | NZ | 247244 | 2/1995 |
| IT | 1196760 | 11/1988 | | NZ | 240855 | 5/1995 |
| IT | 1218991 | 4/1990 | | NZ | 240856 | 6/1995 |
| JP | 55-20517 | 6/1980 | | NZ | 264326 | 9/1995 |
| JP | 58-37357 | 8/1983 | | NZ | 347370 | 10/1995 |
| JP | 58-49595 | 11/1983 | | PH | 27596 | 8/1993 |
| JP | 59-5640 | 2/1984 | | TW | 80103019 | 11/1992 |
| JP | 60-17768 | 5/1985 | | TW | 80109657 | 1/1993 |
| JP | 3-11811 | 2/1991 | | TW | 81108796 | 7/1994 |
| JP | 4-964 | 1/1992 | | WO | WO88/05812 | 8/1988 |
| JP | 4-2566 | 1/1992 | | WO | WO 91/11984 | 8/1991 |
| JP | 4-2567 | 1/1992 | | WO | WO92/04882 | 4/1992 |
| JP | 6-62392 | 2/1992 | | WO | WO 92/10161 | 6/1992 |
| JP | 6-69943 | 9/1992 | | WO | WO92/10162 | 6/1992 |
| JP | 5-60805 | 9/1993 | | WO | WO92/10163 | 6/1992 |
| JP | 5-75722 | 10/1993 | | WO | WO 92/18100 | 10/1992 |
| JP | 5-86367 | 12/1993 | | WO | WO 93/08787 | 5/1993 |
| JP | 6-2653 | 1/1994 | | WO | WO94/01076 | 1/1994 |
| JP | 6-17295 | 3/1994 | | WO | WO94/05256 | 3/1994 |
| JP | 6-23085 | 3/1994 | | WO | WO94/06403 | 3/1994 |
| JP | 6(94)-96715 | 3/1994 | | WO | WO94/06409 | 3/1994 |
| JP | 6-312915 | 8/1994 | | WO | WO94/06410 | 3/1994 |
| JP | 6(94)18770 | 11/1994 | | WO | WO94/07458 | 4/1994 |
| JP | 7-17491 | 3/1995 | | WO | WO94/16676 | 8/1994 |
| JP | 7-26115 | 3/1995 | | WO | WO94/16678 | 8/1994 |
| NZ | 19 4206 | 7/1984 | | WO | WO94/17783 | 8/1994 |
| NZ | 20 5787 | 7/1986 | | WO | WO 94/18935 | 9/1994 |
| NZ | 212928 | 6/1989 | | WO | WO94/26235 | 11/1994 |
| NZ | 2 20643 | 7/1989 | | WO | WO94/27562 | 12/1994 |
| NZ | 238934 | 1/1993 | | WO | WO95/01153 | 1/1995 |
| NZ | 0 530 974 | 3/1993 | | WO | WO95/05157 | 2/1995 |
| NZ | 0237836 | 5/1993 | | WO | WO95/02388 | 4/1995 |
| NZ | 238933 | 7/1993 | | WO | WO 95/09599 | 4/1995 |
| NZ | 237836 | 9/1993 | | WO | WO95/11004 | 4/1995 |
| NZ | 245784 | 8/1994 | | WO | WO95/22311 | 8/1995 |
| NZ | 243257 | 9/1994 | | | | |
| NZ | 242227 | 11/1994 | | | | |

\* cited by examiner

PERSONAL CLEANSING COMPOSITIONS

CROSS-REFERENCE TO RELATED APPLICATION

This application is a divisional application of U.S. application Ser. No. 08/789,593 filed Jan. 24, 1997, now issued as U.S. Pat. No. 6,090,773, which claims the benefit of U.S. Provisional Application No. 60/010,784 filed on Jan. 29, 1996, which is incorporated by reference in its entirety.

BACKGROUND OF THE INVENTION

1. Field of the Invention

This invention relates to conditioning detergent compositions suitable for use in personal cleansing application which not only impart cleansing, wet detangling, dry detangling and manageability properties to hair, but also which are relatively nonirritating and thus suitable for use by young children and adults having sensitive skin and eyes.

2. Description of the Prior Art

In the past, it has been considered desirable to cleanse hair and then to condition it after cleansing. For many years, it was necessary to perform these acts in two separate steps. However, with the advent of so-called "two-in-one" conditioning shampoos, it became possible to condition and cleanse simultaneously. Unfortunately, many of these two-in-one conditioning shampoos and body cleansers have proven to be relatively irritating to the eyes and skin and uncomfortable for use with children or sensitive adults. Therefore, it is an object of this invention to create a conditioning shampoo which has good cleansing ability, excellent conditioning properties and has a low degree of ocular and skin irritation.

SUMMARY OF THE INVENTION

In accordance with this invention, there is provided a detergent composition comprising:

a surfactant portion comprising:
1. a nonionic surfactant:
2. an amphoteric surfactant; and
3. an anionic surfactant; and a conditioner portion comprising at least two cationic conditioning polymers selected from:
1. a cationic cellulose derivative;
2. a cationic guar derivative; and
3. a homopolymer or copolymer of a cationic monomer selected from:
   a. a monomer having the formula

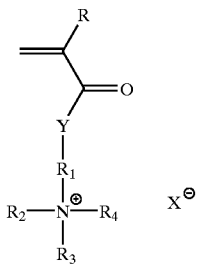

wherein
R is H or $CH_3$,
Y is O or NH,
$R_1$ is an alkylene group having from about 2 to about 6 carbon atoms,
$R_2$, $R_3$ and $R_4$ are each independently an alkyl group or hydroxyalkyl group having from about 1 to about 22 carbon atoms, and
X is a monovalent anion selected from halide and alkyl sulfate having from about 1 to about 4 carbon atoms, or
   b. diallyldimethylammonium chloride.

In accordance with another embodiment of this invention, there is provided a detergent composition comprising, based upon the total weight of the composition:

a. a carboxyalkyl alkylpolyamine amphoteric surfactant of the formula:

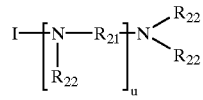

wherein
I is an alkyl or alkenyl group containing from about 8 to about 22 carbon atoms:
$R_{22}$ is a carboxyalkyl group having from about 2 to about 3 carbon atoms:
$R_{21}$ is an alkylene group having from about 2 to about 3 carbon atoms
u is an integer of 1 to 4; and b. an anionic surfactant, except those anionic surfactants of the group consisting of
1) an alkyl sulfate of the formula

R'—$CH_2OSO_3X'$; and 2) an alkylaryl sulfonate of the formula

wherein
R' is an alkyl group having from about 7 to about 14 carbon atoms,
$R'_1$ is an alkyl group having from about 1 to about 12 carbon atoms,
X' is selected from the group consisting of alkali metal ions, alkaline earth metal ions, ammonium ions, and ammonium ions substituted with from about 1 to about 3 substituents; each of the substituents may be the same or different and are selected from the group consisting of alkyl groups having 1 to 4 carbon atoms and hydroxyalkyl groups having from about 2 to about 4 carbon atoms; and c.) optionally a non-ionic surfactant,
with the proviso that if the non-ionic surfactant is omitted and the anionic surfactant is an alkyl ether sulfate of the formula

R'($OCH_2CH_2$)$OSO_3X'$;

then v is greater than or equal to 3.

In accordance with yet another embodiment of this invention, there is provided a detergent composition comprising a. an amidoalkyl sultaine amphoteric surfactant of the formula:

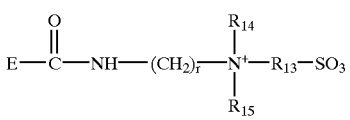

wherein

E is an alkyl group or alkenyl group having from about 7 to about 21 carbon atoms;

$R_{14}$ and $R_{15}$ are each independently an alkyl group or a hydroxyalkyl group having from about 1 to about 4 carbon atoms;

r is an integer from about 2 to about 6; and $R_{13}$ is an alkylene or hydroxyalkylene group having from about 2 to about 3 carbon atoms;

b. an anionic surfactant, except those anionic surfactants of the group consisting of 1. an alkyl sulfate of the formula $R'$—$CH_2OSO_3X'$;

2. an alkyl ether sulfate of the formula $R'(OCH_2CH_2)_vOSO_3X'$; and 3. an alkylaryl sulfonate of the formula

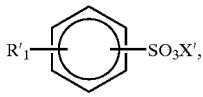

wherein

R' is an alkyl group having from about 7 to about 14 carbon atoms, $R'_1$ is an alkyl group having from about 1 to about 12 carbon atoms, X' is selected from the group consisting of alkali metal ions, alkaline earth metal ions, and ammonium ions, and ammonium ions substituted with from about 1 to about 3 substituents: each of the substituents may be the same or different and are selected from the group consisting of alkyl groups having 1 to 4 carbon atoms and hydroxyalkyl groups having from about 2 to about 4 carbon atoms; and v is an integer from 1 to 5; and c. optionally a non-ionic surfactant.

The composition of this invention, when used in a shampoo or body cleanser, possesses one or more of the following properties: cleansing, wet detangling, dry detangling, manageability, and low degree of ocular irritation.

DETAILED DESCRIPTION OF PREFERRED EMBODIMENTS

In one embodiment of the present invention, the shampoo composition may suitably comprise consist of or consist essentially of an anionic surfactant, an amphoteric surfactant, a non-ionic surfactant, and at least two cationic conditioning polymers. The composition is preferably comprised of, based upon the total weight of the shampoo composition, from about 5 percent to about 20 percent, and more preferably from about 5 percent to about 14 percent of a surfactant portion and, based upon the total weight of the composition, from about 0.01 percent to about 3.0 percent, preferably from about 0.01 percent to about 2.0 percent, more preferably from about 0.01 percent to about 1.0 percent even more preferably from about 0.01 percent to about 0.5 percent, and most preferably from about 0.01 percent to about 0.3 percent of a conditioner portion.

In this embodiment, the surfactant portion of the present invention contains nonionic, amphoteric and anionic surfactants. Preferably the weight ratio between the amphoteric surfactant and the anionic surfactant may range from about 3:1 to about 1:3, and preferably from about 2:1 to about 1:2. The weight ratio of the amphoteric/anionic surfactant combination:non-ionic surfactant may vary widely, and preferably is about 2:1 to about 1:2. The nonionic surfactant is present in an amount, based upon the total weight of the shampoo composition, of from about 0.1 percent to about 10 percent, preferably from about 1 percent to about 10 percent, and more preferably from about 4 percent to about 8 percent. The amphoteric surfactant is present in an amount, based upon the total weight of the shampoo composition, of from about 0.5 percent to about 10 percent, preferably from about 1 percent to about 8 percent, and more preferably from about 2 percent to about 6 percent. The anionic surfactant is present in the shampoo composition in an amount from about 1.0 percent to about 10 percent, preferably from about 1 percent to about 8 percent, and more preferably from about 1 percent to about 6 percent, based on the overall weight of the shampoo composition.

One class of nonionic surfactants useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, a-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units: and (3) has an average of about 1 to about 3 fatty acid residues per mole of polyoxyethylene derivative of polyol ester.

Examples of preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. The alkyl gluocosides have about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

The compositions of the present invention also contain an amphoteric surfactant. As used herein the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Commercially available amphoteric surfactants are suitable for use in the present invention and include, but are not limited to amphocarboxylates, alkyl betaines, amidoalkyl betaines, amidoalkyl sultaines, amphophosphates, phosphobetaines, pyrophosphobetaines, carboxyalkyl alkyl polyamines and mixtures thereof.

Examples of suitable amphocarboxylate compounds include those of the formula:

wherein
  A is an alkyl or alkenyl group having from about 7 to about 21 and preferably from about to about 16 carbon atoms;
  x is an integer of from about 2 to about 6;
  $R_5$ is hydrogen or a carboxyalkyl group containing from about 2 to about 3 carbon atoms, and preferably is hydrogen
  $R_6$ is a hydroxyalkyl group containing from about 2 to about 3 carbon atoms or is a group of the formula:

$$R_8-O-(CH_2)_nCO_2$$

wherein
    $R_8$ is an alkylene group having from about 2 to about 3 carbon atoms and n is 1 or 2; and
  $R_7$ is a carboxyalkyl group containing from about 2 to about 3 carbon atoms; Preferably, the amphocarboxylate compound is an imidazoline surfactant, and more preferably a disodium lauroamphodiacetate, which is commercially available from Mona Chemical Company of Paterson. N.J. under the tradename, "Monateric 949J." When an amphocarboxylate is used in the shampoo composition, it should be present in an amount of about 0.5 percent to about 10 percent and preferably from about 0.5 percent to about 6 percent, based on the overall weight of the composition.

Examples of suitable alkyl betaines include those compounds of the formula:

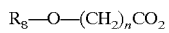

wherein
  B is an alkyl or alkenyl group having from about 8 to about 22, and preferably from about 8 to about 16 carbon atoms;
  $R_9$ and $R_{10}$ are each independently an alkyl or hydroxyalkyl group having from about 1 to about 4 carbon atoms: and
  p is 1 or 2.

A preferred betaine for use in the present invention is lauryl betaine, available commercially from Albright & Wilson, Ltd. of West Midlands, United Kingdom as "Empigen BB/J." If present, the alkyl betaine should be used in an amount, based on the overall weight of the composition, of from about 0.25 percent to about 10 percent, preferably from about 0.25 percent to about 8 percent, and more preferably, from about 0.25 percent to about 5 percent.

Examples of suitable amidoalkyl betaines include those compounds of the formula:

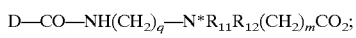

wherein
  D is an alkyl or alkenyl group having from about 7 to about 21, and preferably from about 7 to about 15 carbon atoms;
  $R_{11}$, and $R_{12}$ are each independently an alkyl or hydroxyalkyl group having from about 1 to about 4 carbon atoms:
  q is an integer from about 2 to about 6: and m is 1 or 2.
    A preferred amidoalkyl betaine is cocamidopropyl betaine, available commercially from Goldschmidt Chemical Corporation of Hopewell, Va. under the tradename, "Tegobetaine L7." When present in the shampoo compositions of this invention, the amidoalkyl betaine should be used in an amount of from about 0.25 percent to about 10 percent, preferably from about 0.25 percent to about 8 percent, and more preferably from about 0.25 percent to about 5 percent, based on the overall weight of the composition.

Examples of suitable amidoalkyl sultaines include those compounds of the formula

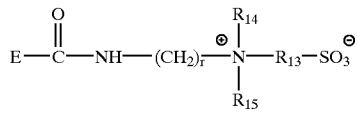

wherein
  E is an alkyl or alkenyl group having from about 7 to about 21, and preferably from about 7 to about 15 carbon atoms;
  $R_{14}$ and $R_{15}$ are each independently an alkyl, or hydroxyalkyl group having from about 1 to about 4 carbon atoms:
  r is an integer from about 2 to about 6; and
  $R_{13}$ is an alkylene or hydroxyalkylene group having from about 2 to about 3 carbon atoms;
  Preferably the amidoalkyl sultaine is cocamidopropyl hydroxysultaine, available commercially from Rhone-Poulenc Inc. of Cranbury, N.J. under the tradename, Mirataine CBS." When present in the shampoo compositions of this invention, it should be used in an amount of from about 0.5 percent to about 10 percent, preferably from about 1.0 percent to about 6 percent, and more preferably from about 1.5 percent to about 5 percent, based on the overall weight of the composition.

Examples of suitable amphophosphate compounds include those of the formula:

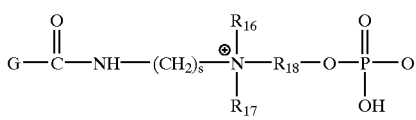

wherein
G is an alkyl or alkenyl group having about 7 to about 21, and preferably from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

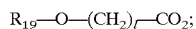

wherein
$R_{19}$ is an alkylene or hydroxyalkylene group having from about 2 to about 3 carbon atoms and
t is 1 or 2; and
$R_{18}$ is an alkylene or hydroxyalkylene group having from about 2 to about 3 carbon atoms.

Preferably the amphophosphate compounds are sodium lauroampho PG-acetate phosphate available commercially from Mona Industries of Paterson, N.J. under the tradename, "Monateric 1023," and those disclosed in U.S. Pat. No. 4,380,637, which is incorporated herein by reference, with sodium lauroampho PG-acetate phosphate being most preferred.

Examples of suitable phosphobetaines include those compounds of the formula:

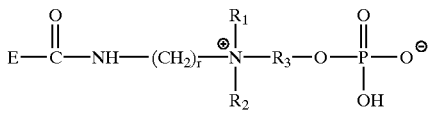

wherein E, r, $R_1$, $R_2$ and $R_3$, are as defined above. Preferably the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

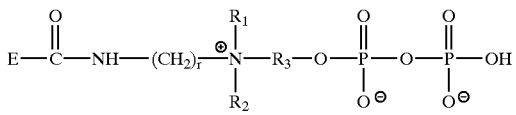

wherein E, r, $R_1$, $R_2$ and $R_3$, are as defined above. Preferably the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

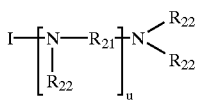

wherein
I is an alkyl or alkenyl group containing from about 8 to about 22, and preferably from about 8 to about 16 carbon atoms;

$R_{22}$ is a carboxyalkyl group having from about 2 to about 3 carbon atoms;

$R_{21}$ is an alkylene group having from about 2 to about 3 carbon atoms and u is an integer from about 1 to about 4.

Preferably the carboxyalkyl alkyl polyamine is sodium carboxymethyl coco polypropylamine available commercially from Akzo Nobel Surface Chemistry under the tradename, "Ampholak 7CX/C." When present in the shampoo compositions of this invention, it should be used in an amount of from about 0.5 percent to about 10 percent, preferably from about 1.0 percent to about 8 percent, and more preferably from about 2.0 percent to about 6.0 percent, based on the overall weight of the composition.

In a preferred embodiment, the amphoteric surfactant portion of the compositions is comprised of a mixture of amphoteric surfactants, such as amphocarboxylate and alkyl betaine, or amphocarboxylate and amidoalkyl betaine. In this embodiment, the amphocarboxylate is present in the shampoo composition in an amount, based upon the total weight of the shampoo composition of from about 0.5 percent to about 9.5 percent and the alkyl betaine or amidoalkyl betaine is present in an amount, based upon the total weight of the shampoo composition, of from about 9.5 percent to about 0.5 percent.

The compositions of this embodiment also contain at least one anionic surfactant. Preferably, the anionic surfactant is selected from the following classes of surfactants:

an alkyl sulfate of the formula

an alkyl ether sulfate of the formula

an alkyl monoglyceryl ether sulfate of the formula

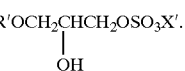

an alkyl monoglyceride sulfate of the formula

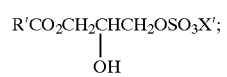

an alkyl monoglyceride sulfonate of the formula

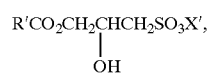

an alkyl sulfonate of the formula

an alkylaryl sulfonate of the formula

an alkyl sulfosuccinate of the formula:

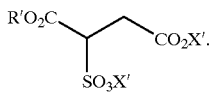

an alkyl ether sulfosuccinate of the formula:

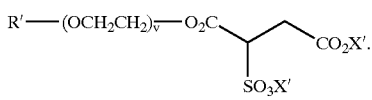

an alkyl sulfosuccinate of the formula:

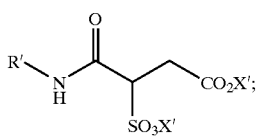

an alkyl amidosulfosuccinate of the formula

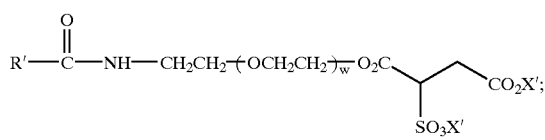

an alkyl carboxylate of the formula:

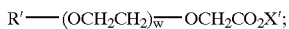

an alkyl amidoethercarboxylate of the formula:

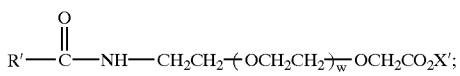

an alkyl succinate of the formula:

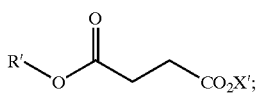

a fatty acyl sarcosinate of the formula:

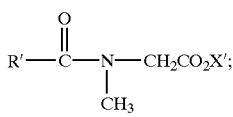

a fatty acyl amino acid of the formula:

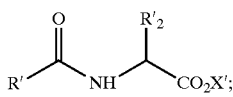

a fatty acyl taurate of the formula:

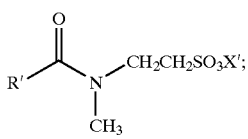

a fatty alkyl sulfoacetate of the formula:

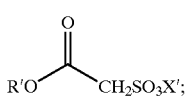

an alkyl phosphate of the formula:

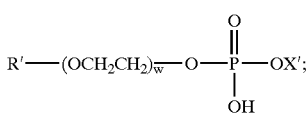

wherein
R' is an alkyl group having from about 7 to about 22, and preferably from about 7 to about 16 carbon atoms, $R'_1$ is an alkyl group having from about 1 to about 18, and preferably from about 8 to about 14 carbon atoms, $R'_2$ is a substituent of a natural or synthetic 1-amino acid.

X' is selected from the group consisting of alkali metal ions, alkaline earth metal ions ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and v is an integer from 1 to 6;

w is an integer from 0 to 20;

and mixtures thereof. Preferably the anionic surfactant is composed of sodium trideceth sulfate, sodium laureth sulfate, disodium laureth sulfosuccinate, or mixtures thereof. Sodium trideceth sulfate is the sodium salt of sulfated ethoxylated tridecyl alcohol that conforms generally to the following formula. $C_{13}H_{27}(OCH_2CH_2)_nOSO_3Na$, where n has a value between 1 and 4, and is commercially available from Stepan Company of Northfield, Ill. under the tradename, "Cedapal TD-403M." Sodium laureth sulfate is available from from Albright & Wilson, Ltd. West Midlands, United Kingdom under the tradename. "Empicol 025117OJ." Disodium laureth sulfosuccinate is available commercially from Albright & Wilson. Ltd. of West Midlands, United Kingdom under the tradename, "Empicol SDD."

In this embodiment, the shampoo composition of the present invention also contains a conditioner portion which is comprised of at least two cationic conditioning polymers. Preferred cationic conditioning polymers are selected from the following:

1. a cationic cellulose derivative;
2. a cationic guar derivative; and
3. a homopolymer or copolymer of a cationic monomer selected from:

a. a monomer having formula I.

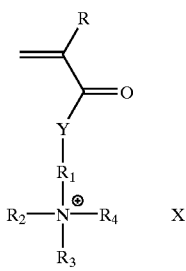

wherein
R is H or CH$_3$,
Y is O or NH,
R$_1$ is an alkylene group having from about 2 to about 6, and preferably from about 2 to about 3 carbon atoms,
R$_2$, R$_3$ and R$_4$ are each independently an alkyl group having from about 1 to about 22, and preferably from about 1 to about 4 carbon atoms, and
X is a monovalent anion selected from halide and alkyl sulfate, or b. diallyldimethylammonium chloride.

The amount of each conditioner component may range, based upon the total weight of the composition, from about 0.01 percent to about 1.0 percent, preferably from about 0.01 percent to about 0.5 percent, and more preferably from about 0.01 to about 0.2 percent.

Preferably, the cationic cellulose derivative is a polymeric quaternary ammonium salt derived from the reaction of hydroxyethyl cellulose with a trimethylammonium substituted epoxide. The material known as Polyquaternium-10, commercially available from Amerchol Corporation of Edison, N.J. as Polymer "JR$_{400}$," is especially useful in this regard.

The cationic guar derivative is preferably a guar hydroxypropyltrimonium chloride, available commercially from Rhone-Poulenc Inc., of Cranbury, N.J. under the tradename, "Jaguar C-17."

Another preferred cationic polymer includes those compounds derived from acrylamidopropyl trimonium chloride which has the formula:

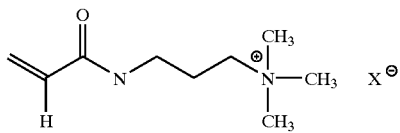

and more preferably is the copolymer of this monomer with acrylamide, the latter of which is available commercially from Allied Colloids, of Suffolk, Va. under the tradename, "Salcare SC60."

Other preferred cationic conditioning polymers are those derived from the monomer diallyldimethylammonium chloride. The homopolymer of this monomer is Polyquaternium-6, which is available commercially form Allied Colloids of Suffolk, Va. under the tradename, "Salcare SC30." The copolymer of diallyldimethylammonium chloride with acrylamide is known as Polyquaternium-7, and is also available from Allied Colloids under the tradename "Salcare SC 10."

In a preferred embodiment, the conditioner portion is a combination of cationic cellulose derivative with a cationic guar derivative. In this embodiment, the cationic cellulose derivative is present in the composition in an amount, based on the overall weight of the shampoo composition, of from about 0.01 percent to about 2 percent, preferably from about 0.05 percent to about 1.0 percent, and more preferably from about 0.05 percent to about 0.3 percent, and the cationic guar derivative is present in an amount, based on the overall weight of the shampoo composition, of from about 0.01 percent to about 1.0 percent, preferably from about 0.05 percent to about 1.0 percent, and more preferably from about 0.05 percent to about 0.3 percent.

In another preferred embodiment, the conditioner portion is comprised of cationic cellulose derivative or cationic guar derivative and a homopolymer or copolymer of the cationic monomer having formula 1. In this embodiment, the cationic cellulose derivative or cationic guar derivative is present in an amount, based on the overall weight of the composition, of from about 0.01 percent to about 0.5 percent, and preferably from about 0.01 percent to about 0.2 percent, and the homopolymer or copolymer of the above monomer is present in an amount, based on the overall weight of the composition of from about 0.01 percent to about 0.5 percent, preferably from about 0.01 percent to about 0.2 percent.

In another preferred embodiment, the conditioner portion is comprised of cationic guar derivative and a homopolymer or copolymer of diallyldimethylammonium chloride. In this embodiment the cationic guar derivative is present in an amount, based on the overall weight of the shampoo composition, of from about 0.01 percent to about 0.5 percent, preferably from about 0.01percent to about 0.2 percent, and the homopolymer or copolymer of diallyldimethylammonium chloride is present in an amount based on the overall weight of the shampoo composition, of from about 0.01 percent to about 0.5 percent, preferably from about 0.01 percent to about 0.2 percent.

In accordance with another embodiment of this invention, there is provided a composition suitably comprised of, consisting of, or consisting essentially of an amphoteric surfactant and an anionic surfactant, with the total amount of surfactants ranging, based upon the total weight of the composition, from about 4 percent to about 20 percent, preferably from about 4 percent to about 15 percent, and more preferably from about 4 percent to about 10 percent. Examples of suitable amphoteric surfactants include those described above and preferably include the above-described carboxyalkyl alkylpolyamines, the amidoalkyl sultaines, and mixtures thereof. Examples of suitable anionic surfactants include those described above and preferably include those anionic surfactants except the anionic surfactant compounds of the group consisting of: 1) the above-described alkyl sulfates or alkylaryl sulfonates when the amphoteric surfactant is the above described carboxyalkyl alkylpolyamine; and 2) the alkyl sulfates, alkyl ether sulfates, and alkylaryl sulfonates when the amphoteric surfactant is the above-described amidoalkyl sultaine.

In this embodiment, the amount of each of the amphoteric surfactant and anionic surfactant used in the composition may range, based upon the total weight of the composition, from about 2 percent to about 10 percent, and preferably from about 2 percent to about 6 percent, respectively. The weight ratio of amphoteric surfactant:anionic surfactant may range from about 3:1 to about 1:3, preferably from about 2:1 to about 1:2, and most preferably from about 1.5:1 to about 1:1.5. Optionally, the composition of this embodiment may contain one or more of the above-mentioned non-ionic surfactants and/or one or more of the above-mentioned cationic conditioners. Preferably, the non-ionic surfactant, if used, is a polyoxyethylene derivative of a polyol ester, more preferably Polysorbate 20, and the preferred cationic conditioner is Polyquaternium 10, guar hydroxypropyltriammonium chloride, acrylamidopropyl trimonium chloride/acrylamide copolymer, and mixtures thereof. The amount of nonionic surfactant used in the composition may range, based upon the total weight of the composition, of from about 0 to about 5 percent, and preferably from about 0.5 percent to about 1 percent. When the nonionic surfactant is used, the weight ratio of amphoteric/anionic surfactant:nonionic surfactant is from about 40:1 to about 2:1 and preferably from about 20:1 to about 10:1. The amount of each cationic conditioner used in the composition may range, based upon the total weight of the composition, from about 0 to about 0.5 percent and preferably from greater than about 0 percent to about 0.3 percent, and more preferably from greater than about 0 percent to about 0.2 percent.

The composition of the present invention may also include one or more optional ingredients nonexclusively including a pearlescent or opacifying agent, a thickening agent, secondary conditioners, humectants, chelating agents, and additives which enhance their appearance, feel and fragrance, such as colorants, fragrances, preservatives, pH adjusting agents, and the like. The pH of the shampoo compositions of this invention is preferably maintained in the range of from about 5 to about 7.5, and more preferably from about 5.5 to about 7.0.

Commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent is present in an amount, based upon the total weight of the composition, of from about 0 percent to about 3 percent, preferably from about 0.25 percent to about 2.5 percent, and more preferably, from about 0.5 percent to about 1.5 percent. Examples of suitable pearlescent or opacifying agents include but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula $$HO-(JO)_a-H$$

wherein
J is an alkylene group having from about 2 to about 3 carbon atoms; and a is 2 or 3;
fatty alcohols containing from about 16 to about 22 carbon atoms; fatty esters of the formula $$KCOOCH_2L$$

wherein K and L independently contain from about 15 to about 21 carbon atoms; inorganic solids insoluble in the shampoo composition, and mixtures thereof.

In a preferred embodiment, the pearlescent or opacifying agent is introduced to the shampoo composition as a preformed, stabilized aqueous dispersion, such as that commercially available from Henkel Corporation of Hoboken, N.J. under the tradename, "Euperlan PK-3000." This material is a combination of glycol distearate (the diester of ethylene glycol and stearc acid), Laureth-4 ($CH_3(CH_2)_{10}OCH_2$ ($OCH_2CH_2)_4OH$) and cocamidopropyl betaine and preferably is in a weight percent ratio of from about 25 to about 30: about 3 to about 15: about 20 to about 25, respectively.

Commercially available thickening agents which are capable of imparting the appropriate viscosity to the conditioning shampoo compositions are suitable for use in this invention. If used the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula $$HO-(CH_2CH_2O)_zH$$

wherein z is an integer from about 3 to about 200: and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename. "PEG 6000 DS".

Commercially available secondary conditioners such as volatile silicones which imparts additional attributes such as gloss to the hair are suitable for use in this invention. Preferably, the volatile silicone conditioning agent has an atmospheric pressure boiling point less than about 220 C. The volatile silicone conditioner is present in an amount of from about 0 percent to about 3 percent, preferably from about 0.25 percent to about 2.5 percent, and more preferably from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Coming Corporation of Midland, Mich. under the tradename, "DC-345" and mixtures thereof, and preferably include cyclomethicone fluids.

Commercially available humectants which are capable of providing moisturization and conditioning properties to the shampoo composition are suitable for use in the present invention. The humectant is present in an amount of from about 0 percent to about 10 percent, preferably from about 0.5 percent to about 5 percent, and more preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol. butylene glycol, dipropylene glycol, and mixtures thereof; 2)polyalkylene glycol of the formula $$HO-(RO)_b-H$$

wherein R" is an alkylene group having from about 2 to about 3 carbon atoms and b is an integer of from about 2 to about 10;

3) polyethylene glycol ether of methyl glucose of formula $$CH_3-C_6H_{10}O_5-(OCH_2CH_2)_c-OH$$

wherein c is an integer from about 5 to about 25;

4) urea; and 5) mixtures thereof, with glycerine being the preferred humectant.

Examples of suitable chelating agents include those which are capable of protecting and preserving the compositions of this invention. Preferably, the chelating agent is EDTA, and more preferably is tetrasodium EDTA available commercially from Dow Chemical Company of Midland. Mich.

under the tradename, "Versene 100XL" and is present in an amount, based upon the total weight of the composition from about 0 to about 0.5 percent, and preferably from about 0.05 percent to about 0.25 percent. Suitable preservatives include Quatemium-15. available commercially as "Dowicil 200" from the Dow Chemical Corporation of Midland, Mich., and are present in the composition in an amount, based upon the total weight of the composition, from about 0 to about 0.2 percent and preferably from about 0.05 percent to about 0.10 percent.

The above described composition may be prepared by combining the desired components in a suitable container and mixing them under ambient conditions in any conventional mixing means well known in the art, such as a mechanically stirred propeller, paddle, and the like. Although the order of mixing is not critical, it is preferable to pre-blend certain components, such as the fragrance and the nonionic surfactant before adding such components into the main mixture.

When a cationic guar conditioner is used, it is also preferable to preblend the cationic guar conditioner with glycerin under ambient conditions, then allow the guar conditioner to be wet-out by the glycerin. Although the time to "wet-out" may vary, typically this time period may range from about 5 minutes to about 30 minutes. Preferably, the guar conditioner:glycerin weight ratio is from about 1:100 to about 1:1, and more preferably from about 1:50 to about 1:5, and most preferably from about 1:15 to about 1:7. The resulting suspension is mixed with water under ambient conditions at a suspension:water weight ratio of from about 1:5 to about 1:20. The resulting water-suspension mixture is then acidified with an amount of acid, preferably citric acid, effective to reduce the pH of the overall composition to a value of about 4.

When using a thickener component, it is also preferable to preblend the desired thickener with from about 5 percent to about 20 percent, based upon the total weight of the composition, of water and preferably at a temperature of from about 60° C. to about 80° C. When processing with a thickener, it is also preferable to reduce the temperature of the overall composition to less than about 45° C. before any pre-formed pearlizer is added thereto.

The detergent composition of the present invention is preferably used in personal cleansing applications nonexclusively including shampoos, gels such as shower gels, baths such as baby baths, and the like.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

All amounts of materials are given in parts by weight based on 100 parts of the overall formulation. unless stated otherwise. The following test procedures were used in the following Examples:

1. Hair Conditioning Properties: Conditioning properties of shampoos are determined by measuring the average energy and force required to comb hair in the wet and dry state after the hair has been washed with a particular shampoo formulation in accordance with the method set forth as follows:

a) Preparation of Hair samples: Human hair tresses are prepared by weighing out about 10–12 grams of virgin brown hair, and binding the cuticle end with a cable tie and hot melt glue. The cuticle end of the bundle is positioned in a binder clip. The hair is fanned out evenly over the width of the binder clip. Hot melt glue is applied along the edge of the binder clip, joining the clip and the hair. Glue is applied to the inside of the clip for further strength. A rubber band is applied to the outside of the clip, to keep the jaws of the clip from separating. The glue is allowed to dry thoroughly. The tress is washed to remove contaminants such as dust or shampoo residue by immersing the tress in methanol for ten seconds and removing the tress and allowing it to air dry. Loose hair is removed. Tangles are removed by combing the tresses with a standard comb or brush. Static charge buildup is removed using a static reducing gun.

The number of trials required for the test is equal to the number of formulations (and suitable controls) under test. The formulations are randomized such that each product is applied to each tress at some point in time. Two shampooings each using about 1 cc of shampoo composition are required. The tress is thoroughly wet under running, 100 F tap water. About 1 cc of a given shampoo composition is applied evenly from top to bottom of the tress. Using the fingers of both hands, the shampoo is rubbed into the hair for approximately 30 seconds to produce lather. The tress is then rinsed thoroughly under running, 100° F. water. The tress is then again washed and rinsed using a second 1 cc sample of product. The tress is then allowed to drip dry for 5 minutes.

The tresses are then suspended from a sturdy ring stand such that they hang freely and have several inches of clearance between the bottom of the tress and the top of the bench.

b) Wet Detangling Energy: A Combing Force Device (CFD), which is a hand held, electromechanical instrument which measures the amount of force or energy required to pass a comb through the hair, is held horizontally in the one hand and tangles are removed from the tresses by starting at the lower portion of the tress and moving the CFD downward. Each successive stroke is started at a point which is higher than the previous stroke. This measurement continues until the CFD passes freely through the entire length of the tress. Once all tangles have been removed, three top-to-bottom strokes complete the detangling measurement. The cumulative energy to detangle the hair tresses is reported as wet detangling energy, in units of gram-seconds (g/sec).

c) Wet Comb Force: After the detangling energy measurement is completed on all tresses, the tresses are measured for wet comb force. A sensor attached to a curling iron measures the twisting, or torsional force of the curling iron as the instrument is moved though the hair. The instrument is passed through the detangled tresses about 25 times. Comb force, expressed in grams is the median force required to pass the comb through the detangled tress.

d) Dry Detangling Energy: After the tresses are blow-dried until they are no longer damp, the detangling procedure set forth in b is repeated using the dry tresses.

e) Dry Comb Force: After the tresses are blow-dried until they are no longer damp and dry detangling energy is determined, the combing procedure set forth in c) is repeated using the dry tresses.

2.) Ocular Irritation Properties: Irritation to the eyes expected for a given formulation is measured in accordance with the Invittox Protocol Number 86, the "Trans-epithelial Permeability (TEP) Assay" as set forth in Invittox Protocol Number 86 (May 1994). In general, the ocular irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier).

Exposure of a layer of MDCK cells grown on a microporous membrane to a test sample is a model for the first event that occurs when an irritant comes in contact with the eye. In vivo the outermost layers of the corneal epithelium form a selectively permeable barrier due to the presence of tight junctions between cells. On exposure to an irritant the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well. Generally, a passing score is reflected in an $EC_{50}$ of 2.2% or higher.

Example 1

Compounding of Shampoo Composition

The following pre-blends were prepared:

Preblend A: 1.5 parts of PEG 6000 DS were mixed with 20 parts deionized water at 65° C. in a mixing vessel until a homogeneous mixture was obtained.

Preblend B: 1.00 part glycerine was added to a mixing vessel. 0.1 part Jaguar C17 was added slowly with agitation and the agitation was continued for 15 minutes. 10.0 parts water were added. 20% citric acid solution was added to adjust the pH of the blend to 4.0, and agitation was continued for an additional 15 minutes.

Preblend C: 1.0 part Atlas G-4280 was mixed with 0.25 parts fragrance.

Preblend D: 0.05 parts Dowicil 200 were blended with 0.15 parts water and the mixture was stirred until solution was obtained.

After charging 25.75 parts water to a mixing vessel, 0.19 parts of Polymer JR-400 was added thereto with maintained agitation until a clear solution was obtained. 12.16 parts Tegobetaine L7, 9.50 parts Cedepal TD-403M, 2.85 Monateric 949J and 5.5 parts Atlas G-4280 were added sequentially to the solution with agitation. After Preblend A, which was maintained at a temperature of 65° C. was added with agitation to the solution, Preblend C was then added thereto with agitation. An additional 1.14 parts of Tegobetaine L7 was then added thereto. 0.18 part Versene 100 XL, 3.21 parts of dye solution, preblend D, 4.00 parts Euperlan PK 3000 and 0.75 parts DC 345 were then added sequentially with agitation thereto. Citric acid solution was added in an amount to adjust the pH of the solution to 6.0. Preblend B was then added with agitation. The pH was then checked and adjusted to 6.0 with additional citric acid solution. The amounts of the ingredients used to make the composition of Example 1 are shown in Table 1 below.

The resulting composition was tested for detangling energy and comb force, and the results are provided in Table 2 below: Ocular Irritation of the resulting composition was also measured and the data are presented in Table 3.

TABLE 1

| Ingredient | INCI Name of Active Ingredient | Example 1 | Example 2 | Comparative Example 1 | Comparative Example 2 |
|---|---|---|---|---|---|
| Atlas G-4280 | PEG-80 Sorbitan Laurate | 6.50 | 6.50 | 6.50 | 6.50 |
| Monateric 949J | Lauroamphoglycinate | 2.85 | 2.85 | 2.85 | 2.85 |
| Tegobetaine L7 | Cocamidopropyl Betaine | 13.30 | 13.30 | 13.30 | 13.30 |
| Cedepal TD-403M | Sodium Trideceth Sulfate | 9.50 | 9.50 | 9.50 | 9.50 |
| Polymer JR 400 | Polyquaternium-10 | 0.19 | 0.19 | 0.19 | — |
| Jaguar C17 | Guar Hydroxypropyltrimonium Chloride | 0.10 | 0.10 | — | 0.10 |
| PEG 6000 DS | PEG-150 Distearate | 1.50 | 1.50 | 1.50 | 1.50 |
| Fragrance | | 0.25 | 0.25 | 0.25 | 0.25 |
| Versene 100XL | Tetrasodium EDTA | 0.18 | 0.18 | 0.18 | 0.18 |
| Color (0.10% aq. sol'n) | | 3.21 | 3.21 | 3.21 | 3.21 |
| Dowicil 200 | Quaternium-15 | 0.05 | 0.05 | 0.05 | 0.05 |
| Euperlan PK 3000 | Glycol Distearate, Laureth-4 and Cocamidopropyl Betaine | 4.00 | 4.00 | 4.00 | 4.00 |
| DC 345 Fluid | Cyclomethicone | 0.75 | — | — | — |
| Citric Acid (20% Sol'n) pH to 5.9–6.2 | Citric Acid | 0.85 | 0.85 | 0.85 | 0.85 |
| Glycerin | Glycerin | 1.00 | 1.00 | 1.00 | 1.00 |
| Deionized Water | Deionized Water | Q.S. to 100 | Q.S. to 100 | Q.S. to 100 | Q.S. to 100 |

Example 2

Compounding of Shampoo Composition Without Cyclomethicone

The procedure of Example 1 was repeated using the ingredients as set forth in Table 1. The resulting composition was tested for detangling energy and comb force, and the results are provided in Table 2 below:

Comparative Example 1

Compounding of Shampoo Composition Without Quar Cationic Conditioner or Cyclomethicone The procedure of Example 1 was repeated using the ingredients as set forth in Table 1. The resulting composition was tested for detangling energy and comb force, and the results are provided in Table 2 below:

Comparative Example 2

Compounding of Shampoo Composition Without Polyquaternium-10 or Cyclomethicone

The procedure of Example 1 was repeated using the ingredients as set forth in Table 1 The resulting composition was tested for detangling energy and comb force, and the results are provided in Table 2 below:

TABLE 2

Detangling Energy and Comb Force Measurements

| Property | Example 1 | Example 2 | Comparative Example 1 | Comparative Example 2 |
|---|---|---|---|---|
| Wet Detangling Energy (gram-seconds) | 2218 ± 457 | 2214 ± 683 | 3458 ± 1264 | 3006 ± 630 |
| Wet Comb Force (grams) | 200 ± 25 | 192 ± 51 | 259 ± 77 | 191 ± 58 |
| Dry Detangling Energy (gram-seconds | 2505 ± 1174 | 3162 ± 1386 | 4025 ± 940 | 2891 ± 909 |
| Dry Comb Force (grams) | 169 ± 70 | 164 ± 79 | 161 ± 59 | 146 ± 66 |

As indicated by the data in Table 2, the formulations of Examples 1 and 2, which contain both Polyquaternium-10 and Guar hydroxypropyltrimonium chloride, exhibit significantly improved wet detangling force (lower detangling energy) than either of Comparative examples 1 or 2, each of which contains only one of the conditioners.

In accordance with prior experience, Polyquaternium-10, when used as the sole conditioner in a shampoo formulation, was known to have imparted dry hair managability benefits to the compositions Similarly, cationic guar compounds have been known to impart wet detangling benefits. Due to the cationic nature of both of these compounds, it was thought that these compounds. when used mixed together, would have competed for the anionic sites on the hair and would thus not have resulted in a shampoo composition exhibiting both improved wet and dry detangling benefits. However, we have unexpectedly found that the combination of cationic cellulose derivatives and cationic guar derivatives in the compositions of this invention imparts superior wet and dry detangling properties to the compositions. More specifically, the wet and dry detangling energy is much lower when using the combination of conditioners of this invention, i.e., cationic guar derivatives and Polyquaternium-10. than if either of the conditioners are used alone.

Example 1 differs from Example 2 in the presence of volatile silicone in formulation. As seen from the data in Table 2, the presence of volatile silicone in Example 1 results in a further reduction in dry detangling energy. Thus, it can be seen that the combination of cationic polymer conditioners and volatile silicone of the compositions of this invention afford both excellent wet detangling and dry detangling benefits.

TABLE 3

TEP Ocular Irritation Results

| Formulation | Mean EC$_{50}$ | Rating |
|---|---|---|
| Formula of Example 1 | 3.94 ± 1.20 | pass |
| Johnson's Baby Shampoo | 3.34 ± 0.64 | pass |
| Pert Plus for Kids Light Conditioning | 0.74 ± 0.23 | fail |
| Pert Plus for Kids Normal Conditioning | 0.81 ± 0.28 | fail |

As indicated above, formulations which exhibit a mean EC$_{50}$ value of 2.2 or higher are deemed to pass the ocular irritation test while those exhibiting an EC$_{50}$ value below 2.2 are deemed to fail the test. As shown in Table 3, the formulation of Example 1 exhibits a passing value, which is on par with Johnson's Baby Shampoo, a commercial shampoo known for its ocular mildness. In contrast, other commercial shampoos, i.e., the Pert Plus products marketed by the Proctor & Gamble Company, fail the test.

Thus, it can be seen from the above Examples that the compositions of the present invention possess superior wet and dry detangling capabilities while retaining low ocular irritation values.

Examples 3–15

Preparation of Cleansing Compositions

The following preferred formulations, as shown in Tables 4–7, were made in accordance with the procedure described in Examples 1 and 2.

TABLE 4

| Ingredient | INCI Name of Active Ingredient | Example 3 | Example 4 | Example 5 |
|---|---|---|---|---|
| Atlas G-4280 | PEG-80 Sorbitan Laurate | 6.50 | 6.50 | 6.50 |
| Monateric 949J | Lauroamphoglycinate | 2.85 | 2.85 | 2.85 |
| Tegobetaine L7 | Cocamidopropyl Betaine | 13.30 | 13.30 | 13.30 |
| Cedepal TD-403M | Sodium Trideceth Sulfate | 9.50 | 9.50 | 9.50 |
| Polymer JR 400 | Polyquatemium-10 | 0.14 | — | 0.10 |
| Jaguar C17 | Guar Hydroxypropyltrimonium Chloride | 0.10 | 0.10 | — |
| Salcare SC 60 | Acrylamidopropyl-trimonium Chloride acrylamide copolymer | — | 0.10 | 0.10 |
| PEG 6000 DS | PEG-150 Distearate | 1.50 | 1.50 | 1.50 |
| Fragrance | | 0.25 | 0.25 | 0.25 |
| Versene 100XL | Tetrasodium EDTA | 0.18 | 0.18 | 0.18 |
| Color (0.10% aq. sol'n) | | 3.21 | 3.21 | 3.21 |
| Dowicil 200 | Quatemium-15 | 0.05 | 0.05 | 0.05 |
| Euperlan PK 3000 | Glycol Distearate, Laureth-4 and Cocamidopropyl Betaine | 4.00 | 4.00 | 4.00 |
| DC 345 Fluid | Cyclomethicone | 0.75 | — | — |
| Citric Acid (20% Sol'n) | Citric Acid | 0.85 | 0.85 | 0.85 |
| pH to 5.9–6.2 | | | | |
| Glycerin | Glycerin | 1.00 | 1.00 | 1.00 |
| Deionized Water | Deionized Water | Q.S. to 100 | Q.S. to 100 | Q.S. to 100 |

TABLE 5

| Ingredient | INCI Name of Active Ingredient | Example 6 | Example 7 | Example 8 | Example 9 |
|---|---|---|---|---|---|
| Tween 20 | Polysorbate 20 | 6.30 | 6.30 | 6.30 | 5.30 |
| Monateric 949-J | Disodium Lauroamphodiacetate | 8.29 | 8.29 | 8.29 | 8.29 |
| Empigen BB/J | Lauryl Betaine | 2.00 | 2.00 | 2.00 | 2.00 |
| Empicol 0251/70-J | Sodium Laureth Sulfate | 4.26 | 4.26 | 4.26 | 4.26 |
| Polymer JR 400 | Polyquatemium-10 | 0.19 | — | 0.10 | 0.19 |
| Jaguar C17 | Guar hydroxypropyl Trimonium Chloride | 0.10 | 0.10 | — | 0.10 |
| Salcare SC60 | Acrylamidopropyltri-monium Chloride acrylamide copolymer | — | 0.12 | 0.10 | — |
| PEG 6000 DS | PEG-150 Distearate | 1.90 | 1.90 | 1.90 | 1.90 |
| Fragrance | | 0.15 | 0.15 | 0.15 | 0.15 |

TABLE 5-continued

| Ingredient | INCI Name of Active Ingredient | Example 6 | 7 | 8 | 9 |
|---|---|---|---|---|---|
| Nervanaid B30 | Tetrasodium EDTA | 0.20 | 0.20 | 0.20 | 0.20 |
| Color 1 (0.2% solution) | | 1.25 | 1.25 | 1.25 | 1.25 |
| Color 2 (0.1% solution) | | 0.30 | 0.30 | 0.30 | 0.30 |
| Genapol 437-X* | Ethylene glycol distearate, cocamidopropyl betaine and cocamide monoethanolamide/ diethanolamide | — | — | — | 2.5 |
| Citric Acid (20% Sol'n) | Citric Acid | 1.25 | 1.25 | 1.25 | 1.25 |
| Dowicil 200 | Quatemium-15 | 0.05 | 0.05 | 0.05 | 0.05 |
| Benzyl Alcohol | Benzyl Alcohol | 0.10 | 0.10 | 0.10 | 0.10 |
| Glycerin | Glycerin | 1.00 | 1.00 | 1.00 | 1.00 |
| Deionized Water | Deionized Water | QS to 100 | QS to 100 | QS to 100 | QS to 100 |

*Genapol 437-X is a commercial product containing about 20% ethylene glycol distearate, about 6% cocamidopropyl betaine and about 5% cocamide monoethanolamide/diethanolamide available from Hoechst AG, Frankfurt, Germany.

TABLE 6

| Ingredient | INCI Name of Active Ingredient | Example 10 | 11 | 12 |
|---|---|---|---|---|
| Tween 20 | Polysorbate 20 | 0.50 | 0.50 | 0.50 |
| Empigen BB/J | Lauryl Betaine | 4.20 | 4.20 | 4.20 |
| Ampholak 7CX/C | Sodium Carboxymethyl Cocopolypropylamine | 13.34 | 13.34 | 13.34 |
| Empicol SDD | Disodium Laureth Sulfosuccinate | 13.79 | 13.79 | 13.79 |
| Polymer JR 400 | Polyquatemium-10 | 0.19 | — | 0.05 |
| Jaguar C17 | Guar hydroxypropyl Trimonium Chloride | 0.10 | 0.10 | — |
| Salcare SC60 | Acrylamidopropyl-trimonium Chloride/ acrylamide copolymer | — | 0.12 | 0.05 |
| PEG 6000 DS (Comiel S.p.A.) | PEG-150 Distearate | 1.95 | 1.95 | 1.95 |
| Fragrance | | 0.14 | 0.14 | 0.14 |
| Versene 100XL | Tetrasodium EDTA | 0.20 | 0.20 | 0.20 |
| Color (0.2% solution) | | 0.23 | 0.23 | 0.23 |
| Citric Acid (20% Sol'n) | Citric Acid | 1.77 | 1.77 | 1.77 |
| Dowicil 200 | Quatemium-15 | 0.05 | 0.05 | 0.05 |
| Glycerin | Glycerin | 1.00 | 1.00 | 1.00 |
| Deionized Water | Deionized Water | QS to 100 | QS to 100 | QS to 100 |

TABLE 7

| Ingredient | INCI Name of Active Ingredient | Example 13 | 14 | 15 |
|---|---|---|---|---|
| Plantaren 2000N | Decyl Glucoside | 3.60 | 3.60 | 3.60 |
| Atlas G-4280 | PEG-80 Sorbitan Laurate | 3.60 | 3.60 | 3.60 |
| Mirataine CBS | Cocamidopropyl Hydroxysultaine | 6.50 | 6.50 | 6.50 |
| Monateric 1023 | Sodium Lauroampho PG-Acetate Phosphate | 1.45 | 1.45 | 1.45 |
| Cedepal SN-303 | Sodium Laureth Sulfate | 3.60 | 3.60 | 3.60 |
| Polymer JR 400 | Polyquatemium-10 | 0.19 | — | 0.10 |
| Jaguar C17 | Guar hydroxypropyl Trimonium Chloride | 0.10 | 0.10 | — |
| Salcare SC60 | Acrylamidopropyltrimonium Chloride acrylamide copolymer | — | 0.12 | 0.10 |
| Aculyn 22 | Acrylates/Steareth-20 Methacrylate Copolymer | 1.10 | 1.10 | 1.10 |
| PEG 6000 DS | PEG-150 Distearate | 0.72 | 0.72 | 0.72 |
| Fragrance | | | | |
| Versene 100XL | Tetrasodium EDTA | 0.05 | 0.05 | 0.05 |
| Color 1 (0.2% solution) | | | | |
| Color 2 (0.1% solution) | | | | |
| Citric Acid (20% Sol'n) | Citric Acid | 0.46 | 0.46 | 0.46 |
| Sodium Hydroxide (20% Sol'n) | Sodium Hydroxide | 0.32 | 0.32 | 0.32 |
| Dowicil 200 | Quatemium-15 | 0.05 | 0.05 | 0.05 |
| Glycerin | Glycerin | 1.00 | 1.00 | 1.00 |
| Deionized Water | Deionized Water | QS to 100 | QS to 100 | QS to 100 |

Selected compositions from Tables 4–7 were evaluated for hair and skin cleansing on human subjects where the compositions were evaluated for their cleansing, conditioning and irritancy properties. Selected compositions were also evaluated by manual washing and combing of tresses. The compositions were found to be satisfactory conditioning personal cleansing compositions.

Examples 16–54

Preparation of Cleansing Compositions

Additional compositions are prepared in accordance with the procedure set forth in Examples 1 and 2 using the components as set forth in Tables 8–13 below.

TABLE 8

| Ingredient | INCI Name of Active Ingredient | Example 16 | 17 | 18 | 19 | 20 | 21 | 22 |
|---|---|---|---|---|---|---|---|---|
| Ampholak 7CX/C | Sodium Carboxymethyl Cocopolypropylamine | 6.67 | 13.34 | 33.35 | 6.67 | 20.25 | 13.34 | 13.34 |
| Empicol SDD | Disodium Laureth Sulfosuccinate | 6.9 | 13.79 | 34.5 | 20.25 | 6.67 | 13.79 | 13.79 |
| Polymer JR 400 | Polyquaternium-10 | — | — | — | — | — | 1.0 | — |
| Jaguar C17 | Guar hydroxypropyl Trimonium Chloride | — | — | — | — | — | — | 0.01 |
| Salcare SC60 | Acrylamidopropyltrimonium Chloride acrylamide copolymer | — | — | — | — | — | — | — |
| PEG 6000 DS (Comiel S.p.A)* | PEG-150 Distearate | * | * | * | * | * | * | * |
| Fragrance |  | 0.14 | 0.14 | 0.14 | 0.14 | 0.14 | 0.14 | 0.14 |
| Versene 100XL | Tetrasodium EDTA | 0.20 | 0.20 | 0.20 | 0.20 | 0.20 | 0.20 | 0.20 |
| Color (0.2% solution) |  | 0.23 | 0.23 | 0.23 | 0.23 | 0.23 | 0.23 | 0.23 |
| Citric Acid (20% Sol'n) | Citric Acid | 1.00 | 1.77 | 3.50 | 1.00 | 1.77 | 3.50 | 3.50 |
| Dowicil 200 | Quaternium-15 | 0.05 | 0.05 | 0.05 | 0.05 | 0.05 | 0.05 | 0.05 |
| Glycerin | Glycerin | 1.00 | 1.00 | 1.00 | 1.00 | 1.00 | 1.00 | 1.00 |
| Deionized Water | Deionized Water | QS to 100 | QS to 100 | QS to 100 | QS to 100 | QS to 100 | QS to 100 | QS to 100 |

*PEG 6000 DS added in quantity sufficient to adjust viscosity to between 500 and 10,000 centipoise

TABLE 9

| Ingredient | INCI Name of Active Ingredient | Example 23 | 24 | 25 | 26 | 27 | 28 | 29 |
|---|---|---|---|---|---|---|---|---|
| Ampholak 7CX/C | Sodium Carboxymethyl Cocopolypropylamine | 13.34 | 13.34 | 13.34 | 13.34 | 13.34 | 13.34 | 13.34 |
| Empicol SDD | Disodium Laureth Sulfosuccinate | 13.79 | 13.79 | 13.79 | 13.79 | 13.79 | 13.79 | 13.79 |
| Tween 20 | Polysorbate 20 | — | — | — | — | 2.0 | 2.0 | 2.0 |
| Polymer JR 400 | Polyquaternium-10 | 0.005 | 0.005 | 0.7 | — | 0.05 | 0.1 | 0.08 |
| Jaguar C17 | Guar hydroxypropyl Trimonium Chloride | 0.005 | — | 0.3 | 0.5 | 0.15 | — | — |
| Salcare SC60 | Acrylamidopropyltrimonium Chloride acrylamide copolymer | — | 0.005 | — | 0.5 | — | 0.4 | 0.04 |
| PEG 6000 DS (Comiel S.p.A)* | PEG-150 Distearate | * | * | * | * | * | * | * |
| Fragrance |  | 0.14 | 0.14 | 0.14 | 0.14 | 0.14 | 0.14 | 0.14 |
| Versene 100XL | Tetrasodium EDTA | 0.20 | 0.20 | 0.20 | 0.20 | 0.20 | 0.20 | 0.20 |
| Color (0.2% solution) |  | 0.23 | 0.23 | 0.23 | 0.23 | 0.23 | 0.23 | 0.23 |
| Citric Acid (20% Sol'n) | Citric Acid | 1.00 | 1.77 | 3.50 | 1.00 | 1.77 | 3.50 | 3.50 |
| Dowicil 200 | Quaternium-15 | 0.05 | 0.05 | 0.05 | 0.05 | 0.05 | 0.05 | 0.05 |
| Glycerin | Glycerin | 1.00 | 1.00 | 1.00 | 1.00 | 1.00 | 1.00 | 1.00 |
| Deionized Water | Deionized Water | QS to 100 | QS to 100 | QS to 100 | QS to 100 | QS to 100 | QS to 100 | QS to 100 |

*PEG 6000 DS added in quantity sufficient to adjust viscosity to between 500 and 10,000 centipoise

TABLE 10

| Ingredient | INCI Name of Active Ingredient | Example 30 | 31 | 32 | 33 | 34 | 35 | 36 |
|---|---|---|---|---|---|---|---|---|
| Mirataine CBS | Cocamidopropyl Hydroxysultaine | 6.67 | 13.34 | 33.35 | 6.67 | 20.25 | 13.34 | 13.34 |
| Empicol SDD | Disodium Laureth Sulfosuccinate | 6.9 | 13.79 | 34.5 | 20.25 | 6.67 | 13.79 | 13.79 |
| Polymer JR 400 | Polyquaternium-10 | — | — | — | — | — | 1.0 | — |
| Jaguar C17 | Guar hydroxypropyl Trimonium Chloride | — | — | — | — | — | — | 0.01 |
| Salcare SC60 | Acrylamidopropyltrimonium Chloride acrylamide copolymer | — | — | — | — | — | — | — |
| PEG 6000 DS* | PEG-150 Distearate | * | * | * | * | * | * | * |
| Fragrance |  | 0.14 | 0.14 | 0.14 | 0.14 | 0.14 | 0.14 | 0.14 |
| Versene 100XL | Tetrasodium EDTA | 0.20 | 0.20 | 0.20 | 0.20 | 0.20 | 0.20 | 0.20 |
| Color (0.2% solution) |  | 0.23 | 0.23 | 0.23 | 0.23 | 0.23 | 0.23 | 0.23 |
| Citric Acid (20% Sol'n) | Citric Acid | 1.00 | 1.77 | 3.50 | 1.00 | 1.77 | 3.50 | 3.50 |
| Dowicil 200 | Quaternium-15 | 0.05 | 0.05 | 0.05 | 0.05 | 0.05 | 0.05 | 0.05 |
| Glycerin | Glycerin | 1.00 | 1.00 | 1.00 | 1.00 | 1.00 | 1.00 | 1.00 |
| Deionized Water | Deionized Water | QS to 100 | QS to 100 | QS to 100 | QS to 100 | QS to 100 | QS to 100 | QS to 100 |

*PEG 6000 DS added in quantity sufficient to adjust viscosity to between 500 and 10,000 centipoise

TABLE 11

| Ingredient | INCI Name of Active Ingredient | Example 37 | 38 | 39 | 40 | 41 | 42 | 43 |
|---|---|---|---|---|---|---|---|---|
| Ampholak 7CX/C | Sodium Carboxymethyl Cocopolypropylamine | 13.34 | 13.34 | 13.34 | 13.34 | 13.34 | 13.34 | 13.34 |
| Empicol SDD | Disodium Laureth Sulfosuccinate | 13.79 | 13.79 | 13.79 | 13.79 | 13.79 | 13.79 | 13.79 |
| Tween 20 | Polysorbate 20 | — | — | — | — | 2.0 | 2.0 | 2.0 |
| Polymer JR 400 | Polyquaternium-10 | 0.005 | 0.005 | 0.7 | — | 0.05 | 0.1 | 0.08 |
| Jaguar C17 | Guar hydroxypropyl Trimonium Chloride | 0.005 | — | 0.3 | 0.5 | 0.15 | — | — |
| Salcare SC60 | Acrylamidopropyltrimonium Chloride acrylamide copolymer | — | 0.005 | — | 0.5 | — | 0.4 | 0.04 |
| PEG 6000 DS (Comiel S.p.A)* | PEG-150 Distearate | * | * | * | * | * | * | * |
| Fragrance | | 0.14 | 0.14 | 0.14 | 0.14 | 0.14 | 0.14 | 0.14 |
| Versene 100XL | Tetrasodium EDTA | 0.20 | 0.20 | 0.20 | 0.20 | 0.20 | 0.20 | 0.20 |
| Color (0.2% solution) | | 0.23 | 0.23 | 0.23 | 0.23 | 0.23 | 0.23 | 0.23 |
| Citric Acid (20% Sol'n) | Citric Acid | 1.00 | 1.77 | 3.50 | 1.00 | 1.77 | 3.50 | 3.50 |
| Dowicil 200 | Quaternium-15 | 0.05 | 0.05 | 0.05 | 0.05 | 0.05 | 0.05 | 0.05 |
| Glycerin | Glycerin | 1.00 | 1.00 | 1.00 | 1.00 | 1.00 | 1.00 | 1.00 |
| Deionized Water | Deionized Water | QS to 100 | QS to 100 | QS to 100 | QS to 100 | QS to 100 | QS to 100 | QS to 100 |

*PEG 6000 DS added in quantity sufficient to adjust viscosity to between 500 and 10,000 centipoise

TABLE 12

| Ingredient | INCI Name of Active Ingredient | Example 44 | 45 | 46 | 47 | 48 | 49 | 50 |
|---|---|---|---|---|---|---|---|---|
| Atlas G-4280 | PEG-80 Sorbitan Laurate | 2.62 | 10.5 | 6.50 | 13.9 | 0.14 | 6.50 | 6.50 |
| Monateric 949J | Lauroamphoglycinate | 1.15 | 4.6 | 2.85 | 2.85 | 2.85 | 0.3 | 5.7 |
| Tegobetaine L7 | Cocamidopropyl Betaine | 5.37 | 21.5 | 13.30 | 13.30 | 13.30 | 1.4 | 26.60 |
| Cedepal TD-403M | Sodium Trideceth Sulfate | 3.84 | 15.35 | 9.50 | 9.50 | 9.50 | 9.50 | 9.50 |
| Polymer JR 400 | Polyquaternium-10 | 0.005 | 0.5 | 0.25 | 0.25 | 0.01 | 0.1 | |
| Jaguar C17 | Guar Hydroxypropyltrimonium Chloride | 0.005 | — | — | 0.5 | 0.01 | 0.1 | 0.10 |
| Salcare SC60 | Acrylamidopropyltrimonium Chloride acrylamide copolymer | — | 0.5 | 0.25 | — | 0.01 | | 0.10 |
| PEG 6000 DS* | PEG-150 Distearate | * | * | * | * | * | * | * |
| Fragrance | | 0.25 | 0.25 | 0.25 | 0.25 | 0.25 | 0.25 | 0.25 |
| Versene 100XL | Tetrasodium EDTA | 0.18 | 0.18 | 0.18 | 0.18 | 0.18 | 0.18 | 0.18 |
| Color (0.10% aq. sol'n) | | 3.21 | 3.21 | 3.21 | 3.21 | 3.21 | 3.21 | 3.21 |
| Dowicil 200 | Quaternium-15 | 0.05 | 0.05 | 0.05 | 0.05 | 0.05 | 0.05 | 0.05 |
| Euperlan PK 3000 | Glycol Distearate, Laureth-4 and Cocamidopropyl Betaine | 4.00 | 4.00 | 4.00 | 4.00 | 4.00 | 4.00 | 4.00 |
| DC 345 Fluid | Cyclomethicone | 0.75 | 0.75 | 0.75 | 0.75 | 0.75 | 0.75 | 0.75 |
| Citric Acid (20% Sol'n) pH to 5.9–6.2 | Citric Acid | 0.85 | 0.85 | 0.85 | 0.85 | 0.85 | 0.85 | 0.85 |
| Glycerin | Glycerin | 1.00 | 1.00 | 1.00 | 1.00 | 1.00 | 1.00 | 1.00 |
| Deionized Water | Deionized Water | Q.S. to 100 | Q.S. to 100 | Q.S. to 100 | Q.S. to 100 | Q.S. to 100 | Q.S. to 100 | Q.S. to 100 |

*PEG 6000 DS added in quantity sufficient to adjust viscosity to between 500 and 10,000 centipoise

TABLE 13

| Ingredient | INCI Name of Active Ingredient | Example 51 | 52 | 53 | 54 |
|---|---|---|---|---|---|
| Atlas G-4280 | PEG-80 Sorbitan Laurate | 6.50 | 6.50 | 6.50 | 6.50 |
| Monateric 949J | Lauroamphoglycinate | 2.85 | 2.85 | 2.85 | 2.85 |
| Tegobetaine L7 | Cocamidopropyl Betaine | 13.30 | 13.30 | 13.30 | 13.30 |
| Cedepal TD-403M | Sodium Trideceth Sulfate | 3.33 | 33.3 | 9.50 | 9.50 |
| Polymer JR 400 | Polyquaternium-10 | 0.10 | 0.10 | 0.10 | |
| Jaguar C17 | Guar Hydroxypropyltrimonium Chloride | — | — | — | 0.10 |
| Salcare SC60 | Acrylamidopropyltrimonium Chloride acrylamide copolymer | 0.10 | 0.10 | — | — |
| Salcare SC30 | Polyquaternium-6 | — | — | — | 0.10 |

TABLE 13-continued

| Ingredient | INCI Name of Active Ingredient | Example 51 | 52 | 53 | 54 |
|---|---|---|---|---|---|
| Salcare SC10 | Polyquaternium-7 | — | — | 0.10 | * |
| PEG 6000 DS* | PEG-150 Distearate | * | * | * | * |
| Fragrance | | 0.25 | 0.25 | 0.25 | 0.25 |
| Versene 100XL | Tetrasodium EDTA | 0.18 | 0.18 | 0.18 | 0.18 |
| Color (0.10% aq. sol'n) | | 3.21 | 3.21 | 3.21 | 3.21 |
| Dowicil 200 | Quaternium-15 | 0.05 | 0.05 | 0.05 | 0.05 |
| Euperlan PK 3000 | Glycol Distearate, Laureth-4 and Cocamidopropyl Betaine | 4.00 | 4.00 | 4.00 | 400 |
| DC 345 Fluid | Cyclomethicone | 0.75 | 0.75 | 0.75 | 0.75 |
| Citric Acid (20% Sol'n) pH to 5.9–6.2 | Citric Acid | 0.85 | 0.85 | 0.85 | 0.85 |
| Glycerin | Glycerin | 1.00 | 1.00 | 1.00 | 1.00 |
| Deionized Water | Deionized Water | Q.S. to 100 | Q.S. to 100 | Q.S. to 100 | Q.S. to 100 |

*PEG 6000 DS added in quantity sufficient to adjust viscosity to between 500 and 10,000 centipoise

Example 55

In Vitro Tests

Samples of shampoo compositions shown in Table 14 were evaluated in in vitro tests. In general, members of a test panel were given a blind sample of each respective formulation in Table 14, as well as a blind sample of commercially available Pert Plus for Kids conditioning shampoo ("Pert Plus"). The members were asked to independently use the samples, in approximately equivalents amounts, to shampoo and condition their hair for a given period of time.

The results of the in vitro tests revealed that formulations of Examples 1 and 5 were rated as parity to Pert Plus with respect to ease of conditioning of hair in the dry and wet states. However, the formulation of Example 1 was preferred relative to Pert Plus for the attribute of speed of detangling. By contrast, the formulation of Comparative Example 3, containing only a single cationic polymeric conditioner, was less preferred than Pert Plus with respect to these attributes. These results further illustrated that the formulations of the present invention containing at least two conditioning polymers demonstrated performance superior to shampoos containing only a single conditioning polymer.

TABLE 14

| Ingredient | INCI Name of Active Ingredient | Example 1 | 5 | Comparative Example 3 |
|---|---|---|---|---|
| Atlas G-4280 | PEG-80 Sorbitan Laurate | 6.50 | 6.50 | 6.50 |
| Monateric 949J | Lauroamphoglycinate | 2.85 | 2.85 | 2.85 |
| Tegobetaine L7 | Cocamidopropyl Betaine | 13.30 | 13.30 | 13.30 |
| Cedepal TD-403M | Sodium Trideceth Sulfate | 9.50 | 9.50 | 9.50 |
| Polymer JR 400 | Polyquaternium-10 | 0.19 | 0.10 | — |
| Jaguar C17 | Guar Hydroxypropyltrimonium Chloride | 0.10 | — | — |
| Salcare SC60 | Acrylamidopropyltrimonium chloride acrylamide copolymer | — | 0.10 | 0.12 |
| PEG 6000 DS | PEG-150 Distearate | 1.50 | 1.50 | 0.50 |
| Fragrance | | 0.25 | 0.25 | 0.25 |
| Versene 100XL | Tetrasodium EDTA | 0.18 | 0.18 | 0.18 |
| Color (0.10% aq. sol'n) | | 3.21 | 3.21 | 3.21 |
| Dowicil 200 | Quaternium-15 | 0.05 | 0.05 | 0.05 |
| Euperlan PK 3000 | Glycol Distearate, Laureth-4 and Cocamidopropyl Betaine | 4.00 | 4.00 | 4.00 |
| DC 345 Fluid | Cyclomethicone | 0.75 | — | — |
| Citric Acid (20% Sol'n) pH to 5.9–6.2 | Citric Acid | 0.85 | 0.85 | 0.85 |
| Glycerin | Glycerin | 1.00 | 1.00 | 1.00 |
| Deionized Water | Deionized Water | Q.S. to 100 | Q.S. to 100 | Q.S. to 100 |

We claim:

1. A personal cleansing composition comprising, based upon the total weight of the composition.:

a) from about 5 percent to about 20 percent of a surfactant portion comprising:
      1. a nonionic surfactant selected from polyoxyethylene derivatives of polyol esters;
      2. an amphoteric surfactant; and
      3. an anionic surfactant;

b) from about 0.01 percent to about 1.0 percent of a conditioner portion comprising at least two cationic conditioning polymers selected from:
      1. a cationic cellulose derivative;
      2. a cationic guar derivative; and
      3. a homopolymer or copolymer of a cationic monomer selected from:

a. a monomer having the formula

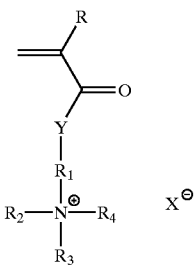

wherein
R is H or CH$_3$,
Y is O or NH,
R$_1$ is an alkylene group having from about 2 to about 6 carbon atoms,
R$_2$, R$_3$ and R$_4$ are each independently an alkyl group or hydroxyalkyl group having from about 1 to about 22 carbon atoms, and
X is a monovalent anion selected from halide and alkyl sulfate having from about 1 to about 4 carbon atoms, or
b. diallyldimethylammonium chloride; and
c) a silicone.

2. A personal cleansing composition comprising
a. an amidoalkyl sultaine amphoteric surfactant of the formula:

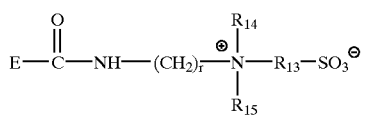

wherein
E is an alkyl group or alkenyl group having from about 7 to about 21 carbon atoms;
R$_{14}$ and R$_{15}$ are each independently an alkyl group or a hydroxyalkyl group having from about 1 to about 4 carbon atoms;
r is an integer from about 2 to about 6; and
R$_{13}$ is an alkylene or hydroxyalkylene group having from about 2 to about 3 carbon atoms;
b. an anionic surfactant,
c. optionally a non-ionic surfactant, and
d. at least two conditioners selected from:
1. a cationic cellulose derivative;
2. a cationic guar derivative; and
3. a homopolymer or copolymer of a cationic monomer selected from:
a. a monomer having the formula

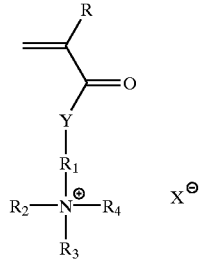

wherein
R is H or CH$_3$,
Y is O or NH,
R$_1$ is an alkylene group having from about 2 to about 6 carbon atoms,
R$_2$, R$_3$ and R$_4$ are each independently an alkyl group or hydroxyalkyl group having from about 1 to about 22 carbon atoms, and
X is a monovalent anion selected from halide and alkyl sulfate having from about 1 to about 4 carbon atoms, or
b. diallyldimethylammonium chloride
wherein surfactants a through c are present in an amount, based upon the total weight of the personal cleansing composition, of from about 4 percent to about 20 percent and each of said conditioners are present in an amount, based upon the total weight of the composition, of from about 0.01 percent to about 0.5 percent.

3. A personal cleansing composition comprising, based upon the total weight of the composition,:
a) from about 5 percent to about 20 percent of a surfactant portion comprising:
1. a nonionic surfactant selected from polyoxyethylene derivatives of polyol esters, alkyl glucosides, and mixtures thereof;
2. an amphoteric surfactant; and
3. an anionic surfactant;
b) from about 0.01 percent to about 1.0 percent of a conditioner portion comprising at least two cationic conditioning polymers selected from:
1. a cationic cellulose derivative;
2. a cationic guar derivative; and
3. a homopolymer or copolymer of a cationic monomer selected from:
a. a monomer having the formula

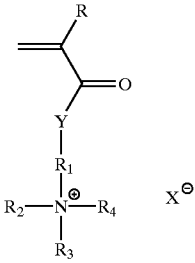

wherein
R is H or CH$_3$,
Y is O or NH,
R$_1$ is an alkylene group having from about 2 to about 6 carbon atoms,
R$_2$, R$_3$ and R$_4$ are each independently an alkyl group or hydroxyalkyl group having from about 1 to about 22 carbon atoms, and
X is a monovalent anion selected from halide and alkyl sulfate having from about 1 to about 4 carbon atoms, or
b. diallyldimethylammonium chloride; and
c) a volatile silicone.

4. The personal cleansing composition of claim 1 wherein the conditioner portion is present in an amount, based upon the total weight of the personal cleansing composition, from about 0.01 percent to about 0.5 percent.

5. The personal cleansing composition of claim 1 wherein the conditioner portion is present in an amount, based upon the total weight of the personal cleansing composition, from about 0.01 percent to about 0.3 percent.

6. The personal cleansing composition of claim 1 wherein the cationic cellulose derivative is polyquaternium-10 and is present in an amount, based upon the total weight of the personal cleansing composition, of from about 0.01 percent to about 0.5 percent.

7. The personal cleansing composition of claim 1 wherein the cationic guar derivative is guar hydroxypropyltrimonium chloride and is present in an amount, based upon the total weight of the personal cleansing composition, of from about 0.01 percent to about 0.5 percent.

8. The personal cleansing composition of claim 1 wherein at least one of the cationic conditioning polymers is a homopolymer or copolymer of a monomer having the formula

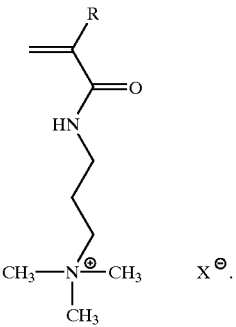

and is present in an amount, based upon the total weight of the personal cleansing composition, of from about 0.01 percent to about 0.5 percent.

9. The personal cleansing composition of claim 1 wherein at least one of the cationic conditioning polymers is an acrylamidopropyltrimonium chloride/acrylamide copolymer and is present in an amount, based upon the total weight of the personal cleansing composition, of from about 0.01 percent to about 0.5 percent.

10. The personal cleansing composition of claim 1 wherein at least one of the cationic conditioning polymers is selected from polyquaternium-6 or polyquaternium-7 and is present in an amount, based upon the total weight of the personal cleansing composition, of from about 0.01 percent to about 0.5 percent.

11. The personal cleansing composition of claim 1 wherein the nonionic surfactant comprises:
a) a polyoxyethylene derivative of a polyol ester
  1. derived from a fatty add containing from about 8 to about 22 carbon atoms and a polyol selected from sorbitol, sorbitan, glucose, I-methyl glucoside, polyglucose having an average of about 1 to about 3 glucose residues, glycerine, pentaerythritol and mixtures thereof,
  2. containing an average of from about 10 to about 120 oxyethylene units, and
  3. having an average of from about 1 to about 3 fatty add residues per molecule of the polyoxyethylene derivative of polyol ester,
b) an alkyl glucoside having an alkyl group containing from about 6 to about 22 carbon atoms and having from about 1 to about 6 glucose residues per molecule of alkyl glucoside, or
c) mixtures thereof,
wherein the nonionic surfactant is present in an amount, based upon the total weight of the personal cleansing composition, of from about 0.1 percent to about 10 percent.

12. The personal cleansing composition of claim 1 wherein the amphoteric surfactant comprises:
a. an amphocarboxylate compound of the formula:

wherein
A is an alkyl or alkenyl group having from about 7 to about 21 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

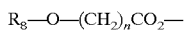

wherein
$R_6$ is an alkylene group having from about 2 to about 3 carbon atoms and
n is 1 or 2; and
$R_7$ is a carboxyalkyl group containing from about 2 to about 3 carbon atoms;
b. an alkyl betaine of the formula:

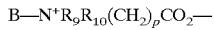

wherein
B is an alkyl or alkenyl group having from about 8 to about 22 carbon atoms;
$R_9$ and $R_{10}$ are each independently an alkyl group or a hydroxyalkyl group having from about 1 to about 4 carbon atoms; and
p is 1 or 2;
c. an amidoalkyl betaine of the formula:

wherein
D is an alkyl or alkenyl group having from about 7 to about 21 carbon atoms;
$R_{11}$ and $R_{12}$ are each independently an alkyl or a hydroxyalkyl group having from about 1 to about 4 carbon atoms;
q is an integer from about 2 to about 6; and
m is 1 or 2;
d. an amidoalkyl sultaine of the formula:

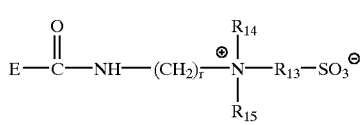

wherein
E is an alkyl group or alkenyl group having from about 7 to about 21 carbon atoms;
$R_{14}$ and $R_{15}$ are each independently an alkyl group or a hydroxyalkyl group having from about 1 to about 4 carbon atoms;
r is an integer from about 2 to about 6; and
$R_{13}$ is an alkylene or hydroxyalkylene group having from about 2 to about 3 carbon atoms;
e. an amphophosphate compound of formula:

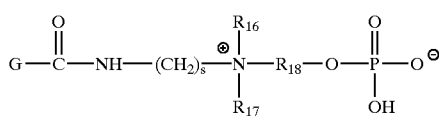

wherein
G is an alkyl group or alkenyl group having about 7 to about 21 carbon atoms;
s is an integer from about 2 to about 6;
$R_{16}$ is hydrogen or a carboxyalkyl group containing from about 2 to about 3 carbon atoms;

$R_{17}$ is a hydroxyalkyl group containing from about 2 to about 3 carbon atoms or is a group of the formula:

wherein
$R_{19}$ is an alkylene group having from about 2 to about 3 carbon atoms and
t is 1 or 2; and
$R_{18}$ is an alkylene or hydroxyalkylene group having from about 2 to about 3 carbon atoms;
f. a phosphobetaine compound of formula

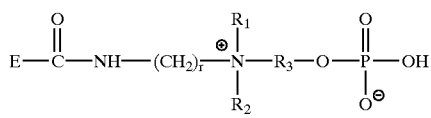

wherein E, r, $R_1$, $R_2$, $R_3$, are as defined above;
g. a pyrophosphobetaine compound of formula

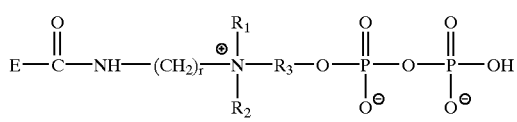

wherein E, r, $R_1$, $R_2$, $R_3$, are as defined above;
h. a carboxyalkyl alkylpolyamine of formula:

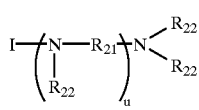

wherein
I is an alkyl or alkenyl group containing from about 8 to about 22 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4; or
i.) mixtures thereof,
wherein the amphoteric surfactant is present in an amount, based upon the total weight of the personal cleansing composition, of from about 0.5 percent to about 10 percent.

13. The personal cleansing composition of claim 12 wherein $R_5$ is hydrogen.

14. The personal cleansing composition of claim 12 wherein the amphoteric surfactant comprises, based upon the total weight of the personal cleansing composition, from
    about 0.5 percent to about 9.5 percent of an alkyl betaine, amidoalkyl betaine, or mixtures thereof, the alkyl group having from about 8 to about 22 carbon atoms; and
    about 0.5 percent to about 9.5 percent of an amphocarboxylate.

15. The personal cleansing composition of claim 1 wherein the anionic surfactant comprises at least one anionic surfactant selected from:
    an alkyl sulfate of the formula

an alkyl ether sulfate of the formula

an alkyl monoglyceryl ether sulfate of the formula

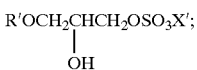

an alkyl monoglyceride sulfate of the formula

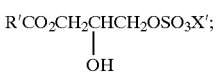

an alkyl monoglyceride sulfonate of the formula

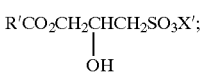

an alkyl sulfonate of the formula

an alkylaryl sulfonate of the formula

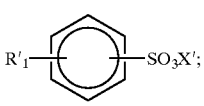

an alkyl sulfosuccinate of the formula:

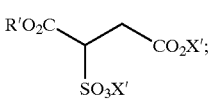

an alkyl ether sulfosuccinate of the formula:

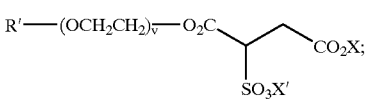

an alkyl sulfosuccinate of the formula:

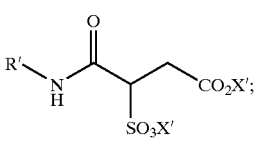

an alkyl amidosulfosuccinate of the formula

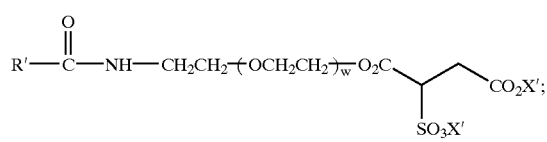

an alkyl carboxylate of the formula:

an alkyl amidoethercarboxylate of the formula:

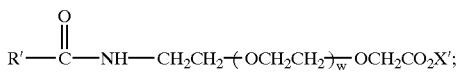

an alkyl succinate of the formula:

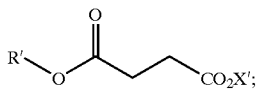

a fatty acyl sarcosinate of the formula:

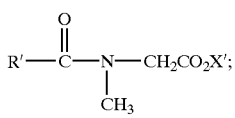

a fatty acyl amino add of the formula:

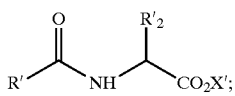

a fatty acyl taurate of the formula:

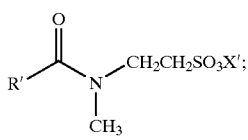

a fatty alkyl sulfoacetate of the formula:

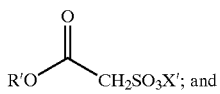

an alkyl phosphate of the formula:

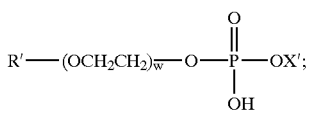

wherein
R' is an alkyl group having from about 7 to about 22 carbon atoms,
$R'_1$ is an alkyl group having from about 1 to about 18 carbon atoms,
$R'_2$ is a substituent of a natural or synthetic α-amino add,
X' is selected from the group consisting of alkali metal ions, alkaline earth metal ions, ammonium ions, and ammonium ions substituted with from about 1 to about 3 substituents, each of the substituents may be the same or different and are selected from alkyl groups having from 1 to 4 carbon atoms and hydroxyalkyl groups having from about 2 to about 4 carbon atoms and
v is an integer from 1 to 6;
w is an integer from 0 to 20;

wherein the anionic surfactant is present in an amount, based upon the total weight of the personal cleansing composition of from about 1 percent to about 10 percent.

16. The personal cleansing composition of claim 1 further comprising a pearlescent or opacifying agent selected from:
   a) mono or diesters of
      1) a fatty add having from about 16 to about 22 carbon atoms and
      2) ethylene glycol or propylene glycol;
   b) mono or diesters of
      1) a fatty add having from about 16 to about 22 carbon atoms and
      2) a polyalkylene glycol of the formula

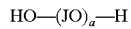

wherein
      J is an alkylene group having from about 2 to about 3 carbon atoms; and
      a is 2 or 3;
   c) fatty alcohols containing from about 16 to about 22 carbon atoms;
   d) fatty esters of the formula

wherein K and L independently are alkyl or alkenyl groups having from about 15 to about 21 carbon atoms;
   e) inorganic solids insoluble in the personal cleansing composition, and
   f) mixtures thereof,
wherein the pearlescent or opacifying agent is present in an amount, based upon the total weight of the personal cleansing composition, of from about 0.25 percent to about 2.5 percent.

17. The personal cleansing composition of claim 16 wherein the inorganic solid is comprised of mica, titanium dioxide, and mixtures thereof.

18. The personal cleansing composition of claim 1 further comprising a humectant selected from:
   a) water soluble liquid polyols selected from glycerine, propylene glycol, hexylene glycol, butylene glycol, dipropylene glycol, and mixtures thereof;
   b) polyalkylene glycol of the formula

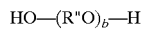

wherein
      R" is an alkylene group having from about 2 to about 3 carbon atoms and
      b is an integer of from about 2 to about 10;
   c) polyethylene glycol ether of methyl glucose of formula

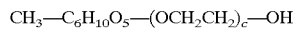

wherein c is an integer from about 5 to about 25;
   d) urea; or
   e) mixtures thereof,
wherein the humectant is present in an amount, based upon the total weight of the personal cleansing composition, of from about 0.5 percent to about 5 percent.

19. The personal cleansing composition of claim 1 further comprising a thickener comprised of:
   a.) mono or diesters of
      1) polyethylene glycol of formula

wherein
z is an integer from about 3 to about 200; and
2) fatty adds containing from about 16 to about 22 carbon atoms;
b.) fatty add esters of ethoxylated polyols;
c.) ethoxylated derivatives of mono and diesters of fatty adds and glycerine;
d.) hydroxyalkyl cellulose;
e.) alkyl cellulose;
f.) hydroxyalkyl alkyl cellulose; and
g) mixtures thereof;
wherein the thickener is present in an amount sufficient to provide the personal cleansing composition with a Brookfield viscosity between about 500 centipoise to about 10,000 centipoise.

20. The personal cleansing composition of claim 1 further comprising a volatile silicone-based conditioner selected from polydimethylsiloxane, polydimethylcyclosiloxane, hexamethyldisiloxane, and mixtures thereof, wherein the silicone-based conditioner is present in an amount, based upon the total weight of the personal cleansing composition, of from about 0.25 percent to about 2.5 percent and has an atmospheric pressure boiling point less than about 220° C.

21. The personal cleansing composition of claim 1 further comprising one or more additives comprising colorants, fragrances, preservatives, pH adjusting agents, and mixtures thereof.

22. The personal cleansing composition of claim 1 wherein the personal cleansing composition has a pH in the range of about 5 to about 7.5.

23. The personal cleansing composition of claim 11 wherein the pearlescent or opacifying agent is added to the personal cleansing composition as a preformed, stabilized aqueous dispersion.

24. The personal cleansing composition of claim 1 wherein the conditioner portion comprises a mixture of Polyquaternium-10 and guar hydroxypropyltrimonium chloride.

25. The personal cleansing composition of claim 1 wherein the conditioner portion comprises
   a. Polyquaternium-10 or guar hydroxypropyltrimonium chloride, and
   b. a homopolymer or copolymer of a cationic monomer having the formula

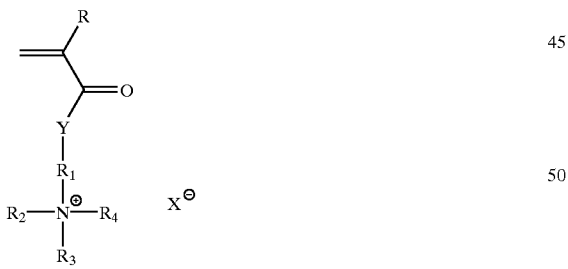

wherein
R is H or CH$_3$,
Y is O or NH,
R$_1$ is an alkylene group having from about 2 to about 3 carbon atoms,
R$_2$, R$_3$ and R$_4$ are each independently an alkyl group having from about 1 to about 4 carbon atoms, and
X is a monovalent anion selected from halide and alkyl sulfate.

26. The personal cleansing composition of claim 1 wherein the conditioner portion comprises a mixture of guar hydroxypropyltrimonium chloride and a homopolymer or copolymer of diallyldimethylammonium chloride.

27. A conditioning personal cleansing composition comprising, based upon the total weight of the personal cleansing composition:
a. from about 1 percent to about 10 percent of nonionic surfactants comprising:
   1) a polyoxyethylene derivative of a polyol ester
      a. derived from a fatty add containing from about 8 to about 22 carbon atoms and a polyol selected from sorbitol, sorbitan, glucose, I-methyl glucoside, polyglucose having an average of about 1 to about 3 glucose residues, glycerine, pentaerythritol and mixtures thereof,
      b. containing an average of from about 10 to about 120 oxyethylene units, and
      c. having an average of from about 1 to about 3 fatty add residues per molecule of the polyoxyethylene derivative of polyol ester,
   2) an alkyl glucoside having an alkyl group containing from about 6 to about 22 carbon atoms and having from about 1 to about 6 glucose residues per molecule of alkyl glucoside, or
   3) mixtures thereof, and
b. from about 0.5 percent to about 10 percent of one or more amphocarboxylate amphoteric surfactants of the formula:

wherein
A is an alkyl or alkenyl group having from about 7 to about 21 carbon atoms;
x is an integer of from about 2 to about 6;
R$_5$ is hydrogen or a carboxyalkyl group containing from about 2 to about 3 carbon atoms;
R$_6$ is a hydroxyalkyl group containing from about 2 to about 3 carbon atoms or a group of the formula:

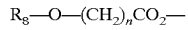

wherein
R$_8$ is an alkylene group having from about 2 to about 3 carbon atoms and
n is 1 or 2; and
R$_7$ is a carboxyalkyl group containing from about 2 to about 3 carbon atoms,
c. from about 0.5 percent to about 10 percent of one or more betaine amphoteric surfactants selected from:
   1) an alkyl betaine of the formula:

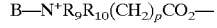

wherein
   B is an alkyl or alkenyl group having from about 8 to about 22 carbon atoms;
   R$_9$ and R$_{10}$ are each independently an alkyl group or a hydroxyalkyl group having from about 1 to about 4 carbon atoms; and
   p is 1 or 2; or
   2) an amidoalkyl betaine of the formula:

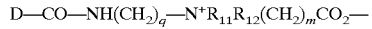

wherein
   D is an alkyl or alkenyl group having from about 7 to about 21 carbon atoms;
   R$_{11}$ and R$_{12}$ are each independently an alkyl group or a hydroxyalkyl group having from about 1 to about 4 carbon atoms;
   q is an integer from about 2 to about 6; and
   2 m is 1 or 2;

d. from about 1 percent to about 10 percent of one or more anionic alkyl ether sulfate surfactants of the formula R'(OCH$_2$CH$_2$)$_v$OSO$_3$X', wherein
R' is an alkyl or alkenyl group having from about 7 to about 22 carbon atoms,
X' is selected from the group consisting of alkali metal ions, alkaline earth metal ions, ammonium ions, ammonium ions substituted with from 1 to 3 substituents, each of the substituents may be the same or different and are selected from alkyl groups having from about 1 to about 4 carbon atoms and hydroxyalkyl groups having from about 2 to about 4 carbon atoms, and
v is an integer from 1 to 6;
e. from about 0.01 percent to about 0.5 percent of Polyquaternium-10; and
f. from about 0.01 percent to about 0.5 percent of guar hydroxypropyltrimonium chloride;
wherein the surfactants in a through d are present in an amount, based upon the total weight of the personal cleansing composition, from about 5 percent to about 20 percent.

28. The personal cleansing composition of claim 27 further comprising from about 0.25 percent to about 2.5 percent, based upon the total weight of the personal cleansing composition, of a pearlescent or opacifying agent comprising a diester of
a. a fatty add having from about 16 to about 22 carbon atoms; and
b. ethylene glycol or propylene glycol.

29. The personal cleansing composition of claim 27 further comprising from about 0.5 percent to about 5 percent, based upon the total weight of the personal cleansing composition, of a humectant comprising glycerine.

30. The personal cleansing composition of claim 27 further comprising a thickener comprising a diester of
a. polyethylene glycol of formula HO—(CH$_2$CH$_2$O)$_z$—H wherein z is an integer from 3 to 200; and
b. a fatty add containing from about 16 to about 22 carbon atoms,
wherein the thickener is present in an amount sufficient to provide the personal cleansing composition with a Brookfield viscosity between about 500 centipoise to about 10,000 centipoise.

31. The personal cleansing composition of claim 27 further comprising, based upon the total weight of the personal cleansing composition, of from about 0.25 percent to about 2.5 percent of a silicone-based conditioner comprised of polydimethylsiloxane, polydimethylcyclosiloxane, hexamethyldisiloxane, and mixtures thereof.

32. The personal cleansing composition of claim 27 further comprising additives comprised of colorants, fragrances, preservatives, pH adjusting agents, and mixtures thereof.

33. The personal cleansing composition of claim 27 wherein the personal cleansing composition has a pH of from about 5 to about 7.5.

34. The personal cleansing composition of claim 28 wherein the pearlescent or opacifying agent is added to the personal cleansing composition as a preformed, stabilized aqueous dispersion.

35. The personal cleansing composition of claim 31 wherein the silicone-based conditioner comprises a volatile silicone compound having an atmospheric pressure boiling point of less than about 220° C.

36. A personal cleansing composition comprising, based upon the total weight of the personal cleansing composition:
from about 5 percent to about 20 percent of a surfactant portion comprising:
1. a nonionic surfactant;
2. an amphoteric surfactant; and
3. an anionic surfactant; and
from about 0.01 percent to about 1.0 percent of a conditioner portion comprising at least two cationic conditioning polymers.

37. A conditioning personal cleansing composition comprising, based upon the total weight of the personal cleansing composition:
a. from about 2 percent to about 10 percent of a polyoxyethylene derivative of polyol ester nonionic surfactant derived from
1) a polyol comprised of sorbitol, sorbitan, and mixtures thereof, and
2) lauric add,
containing an average of from about 20 to about 80 oxyethylene units per molecule of a polyoxyethylene derivative of polyol ester, and
having an average of from about 1 to about 2 lauric add residues per molecule of a polyoxyethylene derivative of polyol ester, and mixtures thereof;
b. from about 0.5 percent to about 5 percent of an amphocarboxylate amphoteric surfactant of the formula A—CONH(CH$_2$)$_x$N$^+$R$_5$R$_6$R$_7$ wherein
A is an alkyl group having about 11 carbon atoms,
x is 2,
R$_5$ is hydrogen,
R$_6$ is a group of the formula R$_8$—O—(CH$_2$)$_n$CO$_2$— wherein
R$_8$ is a 2 carbon alkylene group; and
n is 1; and
R$_7$ is a carboxymethyl group, and mixtures thereof;
c. from about 0.5 percent to about 8 percent of a betaine surfactant selected from:
1) an alkyl betaine of the formula

B—N$^+$R$_9$R$_{10}$CH$_2$CO$_2$— wherein B is a lauryl group having 12 carbon atoms, and
R$_1$ and R$_2$ are each methyl groups,
2) an amidoalkyl betaine of the formula D—CO—NH(CH$_2$)$_q$—N$^+$R$_{11}$R$_{12}$CH$_2$CO$_2$— wherein
DCO represents a fatty add derived from coconut oil,
q is 3 and
R$_{11}$ and R$_{12}$ are each methyl groups, and
3) mixtures thereof;
d. from about 2 percent to about 8 percent of an alkyl ether sulfate anionic surfactant of the formula R'(OCH$_2$CH$_2$)$_v$OSO$_3$X', wherein
R' is an alkyl group having from about 12 to about 13 carbon atoms, X' is a sodium ion; and v is an integer from 1 to 4, and mixtures thereof;

e. from about 0.01 percent to about 0.3 percent of Polyquaternium-10;

f from about 0.01 percent to about 0.3 percent of guar hydroxypropyltrimonium chloride;

wherein the surfactants a through d are present in an amount, based upon the total weight of the personal cleansing composition, of from about 5 percent to about 20 percent.

38. The personal cleansing composition of claim 37 further comprising, based upon the total weight of the personal cleansing composition, from about 0.5 percent to about 2 percent of pearlescent or opacifying agent comprising ethylene glycol distearate.

39. The personal cleansing composition of claim 37 further comprising, based upon the total weight of the personal cleansing composition, from about 0.25 percent to about 1.5 percent of a volatile silicone-based conditioner comprising polydimethylcyclosiloxane, wherein the silicone-based conditioner has an atmospheric pressure boiling point of less than about 220° C.

40. The personal cleansing composition of claim 37 further comprising one or more additives comprised of colorants, fragrances, preservatives, pH adjusting agents, and mixtures thereof.

41. The personal cleansing composition of claim 37 wherein the personal cleansing composition has a pH of from about 5 to about 7.5.

42. The personal cleansing composition of claim 37 further comprising a. from about 0.5 percent to about 3 percent of a humectant comprising glycerine, and/or b. a thickener comprising a stearate diester of polyethylene glycol of the formula $$HO-(CH_2CH_2O)_z-H$$

wherein z is about 150 wherein the thickener is present in an amount sufficient to provide the personal cleansing composition with a Brookfield viscosity between about 500 centipoise to about 10,000 centipoise.

43. The personal cleansing composition of claim 38 wherein the pearlescent or opacifying agent is added to the personal cleansing composition as a preformed, stabilized aqueous dispersion.

44. The personal cleansing composition of claim 37 wherein said personal cleansing composition contains, based upon the total weight of the personal cleansing composition, A. from about 4 percent to about 5 percent of the nonionic surfactant, B. from about 0.5 percent to about 1.5 percent of the amphocarboxylate amphoteric surfactant, C. from about 3 percent to about 5 percent of the cocamidopropyl betaine of the formula $$D-CO-NH(CH_2)_q-N^+R_{11}R_{12}CH_2CO_2-$$

wherein

DCO represents the fatty acid derived from coconut oil, q is 3 and $R_{11}$ and $R_{12}$ are each methyl groups, D. from about 2.5 percent to about 3.5 percent of a sodium trideceth sulfate anionic surfactant having the formula $$R'(OCH_2CH_2)_vOSO_3X'$$

wherein R' is an alkyl group having 13 carbon atoms, X' is sodium ion and v is an integer from 1 to 4, E. from about 0.01 percent to about 0.3 percent of Polyquaternium-10, and F. from about 0.01 percent of about 0.3 percent of guar hydroxypropyltrimonium chloride, and wherein the personal cleansing composition has a pH of from about 5 to about 7.5.

45. The personal cleansing composition of claim 44 further comprising ethylene glycol distearate in an amount, based upon the total weight of the personal cleansing composition, of from about 0.5 percent to about 1.5 percent.

46. The personal cleansing composition of claim 45 further comprising in an amount, based upon the total weight of the personal cleansing composition, from about 0.5 percent to about 1 percent of a volatile silicone-based conditioner having a boiling point less that about 220° C.

47. The personal cleansing composition of claim 37 comprised of, based upon the total wieght of the personal cleansing composition:

A. from about 4 percent to about 8 percent of the nonionic surfactant,

B. from about 1.5 percent to about 3 percent of the amphocarboxylate amphoteric surfactant, C. from about 0.25 percent to about 2.5 percent of lauryl betaine of the formula $$B-N^+R_9R_{10}CH_2CO_2-$$

wherein

B is a lauryl group and $R_9$ and $R_{10}$ are each methyl groups,

D. from about 2 percent to about 4 percent of a sodium laureth sulfate anionic surfactant having the formula $$R'(OCH_2CH_2)_vOSO_3X'$$

wherein

R' is a lauryl group,

X' is sodium ion and v is an integer from 1 to 4,

E. from about 0.01 percent to about 0.3 percent of polyquaternium-10,

F. from about 0.01 percent to about 0.3 percent of a guar hydroxypropyltrimonium chloride, wherein the personal cleansing composition has a pH of from about 5 to about 7.5.

48. The personal cleansing composition of claim 47 further comprising ethylene glycol distearate in an amount, based upon the weight of the personal cleansing composition, of from about 0.5 percent to about 1.5 percent.

49. The personal cleansing composition of claim 48 further comprising a volatile silicone-based conditioner having a boiling point less that about 220° C. in an amount, based upon the total weight of the personal cleansing composition, of from about 0.5 percent to about 1.0 percent.

50. A conditioning personal cleansing composition comprising, based upon the total weight of the personal cleansing composition:

A. from about 5 percent to about 20 percent of a surfactant portion comprising, based upon the total weight of the personal cleansing composition, of 1. about 2.0 percent to about 8 percent of a nonionic surfactant comprising a polyoxyethylene derivative of polyol ester, an alkyl glucoside wherein the alkyl group contains from about 8 to about 14 carbon atoms, or mixtures thereof;

2. about 1 to about 6 percent, of an amidoalkyl sultaine amphoteric surfactant; and 3. from about 1 percent to about 6 percent of an alkyl ether sulfate anionic surfactant; and B. from about 0.01 percent to about 1.0 percent of a conditioner portion comprising at least two cationic conditioning polymers selected from:
1. a cationic cellulose derivative;
2. a cationic guar derivative; and
3. a homopolymer or copolymer of a cationic monomer selected from:
a. a monomer having the formula

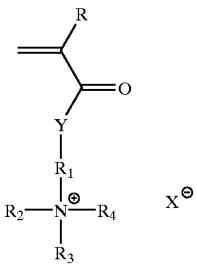

wherein
R is H or $CH_3$,
Y is O or NH,
$R_1$ is an alkylene group having from about 2 to about 3 carbon atoms,
$R_2$, $R_3$ and $R_4$ are each independently an alkyl group having from about 1 to about 4 carbon atoms, and
X is a monovalent anion selected from halide and alkyl sulfate, or
b. diallyldimethylammonium chloride.

51. The personal cleansing composition of claim 50 wherein the conditioner portion is present in an amount of from about 0.01 percent to about 0.3 percent, based upon the total weight of the composition.

52. The personal cleansing composition of claim 50 wherein
the nonionic surfactant is a mixture of decyl glucoside and polyoxyethylene sorbitan monolaurate;
the amphoteric surfactant is cocamidopropyl hydroxysultaine; and
the anionic surfactant is sodium laureth sulfate.

53. The personal cleansing composition of claim 50 which further comprises a thickener in an amount sufficient to provide the personal cleansing composition with a Brookfield viscosity between about 500 centipoise and about 10,000 centipoise, said personal cleansing composition having a pH between about 5 and about 7.5.

54. A conditioning personal cleansing composition comprising, based upon the total weight of the personal cleansing composition:
A. from about 5 percent to about 20 percent a surfactant portion comprising, based upon the total weight of the personal cleansing composition, from:
1. about 0.1 percent to about 8 percent of a nonionic surfactant comprised of
a. a polyoxyethylene derivative of polyol ester;
b. an alkyl glucoside, the alkyl group having from about 8 to about 14 carbon atoms; or
c. mixtures thereof;
2. about 2 percent to about 6 percent of a carboxyalkyl alkyl polyamine amphoteric surfactant of the formula:

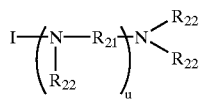

wherein
I is an alkyl or alkenyl group containing from about 8 to about 22 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4;
3. from about 2 percent to about 8 percent of an anionic surfactant selected from an alkyl ether sulfosuccinate, alkyl ether sulfate, or mixtures thereof, the alkyl group having from about 8 to about 14 carbon atoms; and B. about 0.01 percent to about 1.0 percent of a conditioner portion comprising at least two cationic conditioning polymers selected from:
1. a cationic cellulose derivative;
2. a cationic guar derivative;
3. a homopolymer or copolymer of a cationic monomer selected from:
a. a monomer having the formula

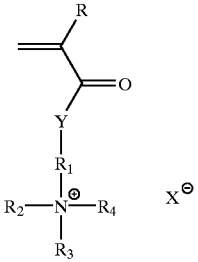

wherein
R is H or $CH_3$,
Y is O or NH,
$R_1$ is an alkylene group having from about 2 to about 6 carbon atoms,
$R_2$, $R_3$ and $R_4$ are each independently an alkyl group or a hydroxyalkyl group having from about 1 to about 22 carbon atoms, and
X is a monovalent anion selected from halide and alkyl sulfate having from 1 about to about 4 carbon atoms, or
b. diallyldimethylammonium chloride.

55. The personal cleansing, composition of claim 54 wherein the conditioner portion is present in an amount, based upon the total weight of the composition, of from about 0.01 percent to about 0.3 percent.

56. The personal cleansing composition of claim 54 wherein
the nonionic surfactant is polyoxyethylene sorbitan monolaurate;
the amphoteric surfactant is sodium carboxymethyl coco polypropylamine; and
the anionic surfactant is disodium laureth sulfosuccinate.

57. The personal cleansing composition of claim 54 which further comprises;
A. a thickener in an amount sufficient to provide the personal cleansing composition with a Brookfield viscosity between about 500 centipoise and about 10,000 centipoise; and/or B. from about 0.5 to about 2.5 percent by weight, based upon the total weight of the personal cleansing composition, of lauryl betaine;

said personal cleansing composition having a pH between about 5 and about 7.5.

58. A personal cleansing composition comprising:

a. an carboxyalkyl alkylpolyamine amphoteric surfactant of the formula:

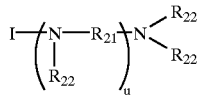

wherein

I is an alkyl or alkenyl group containing from about 8 to about 22 carbon atoms;

$R_{22}$ is a carboxyalkyl group having from about 2 to about 3 carbon atoms;

u is an integer from 1 to 4;

$R_{21}$ is an alkylene group having from about 2 to about 3 carbon atoms and b. an anionic surfactant, except those anionic surfactants of the group consisting of 1) an alkyl sulfate of the formula

2) an alkylaryl sulfonate of the formula

wherein

R' is an alkyl group having from about 7 to about 14 carbon atoms, $R'_1$ is an alkyl group having from about 1 to about 12 carbon atoms, X' is selected from the group consisting of alkali metal ions, alkaline earth metal ions and ammonium ions, and ammonium ions substituted with from about 1 to about 3 substituents; each of the substituents may be the same or different and are selected from the group consisting of alkyl groups having 1 to 4 carbon atoms and hydroxyalkyl groups having from about 2 to about 4 carbon atoms; and c.) a non-ionic surfactant, and d.) a silicone, with the proviso that if the non-ionic surfactant is omitted and the anionic surfactant is an alkyl ether sulfate of the formula

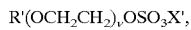

then v is greater than or equal to 3.

59. The personal cleansing composition of claim 58 wherein said amphoteric surfactant is sodium carboxymethyl coco polypropylamine or mixtures thereof.

60. The personal cleansing composition of claim 58 wherein the anionic surfactant is an alkyl ether sulfosuccinate of the formula:

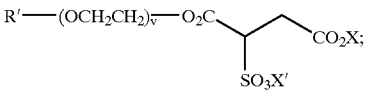

wherein

R' is an alkyl group having from about 7 to about 22 carbon atoms,

X' is selected from the group consisting of alkali metal ions, alkaline earth metal ions, ammonium ions, and ammonium ions substituted with from about 1 to about 3 substituents, each of the substituents may be the same or different and are selected from alkyl groups having from 1 to 4 carbon atoms and hydroxyalkyl groups having from about 2 to about 4 carbon atoms and v is an integer from 1 to 6 or mixtures thereof.

61. The personal cleansing composition of claim 58 wherein the surfactants a through c are present in an amount, based upon the total weight of the personal cleansing composition, of from about 4 percent to about 20 percent.

62. The personal cleansing composition of claim 58 wherein the weight ratio of said amphoteric surfactant to said anionic surfactant ranges from about 1:3 to about 3:1.

63. The personal cleansing composition of claim 58 further comprising at least one conditioner selected from:

1. a cationic cellulose derivative;
2. a cationic guar derivative; and
3. a homopolymer or copolymer of a cationic monomer selected from:
   a. a monomer having the formula

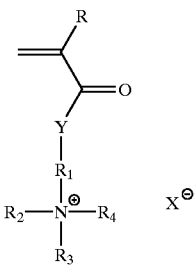

wherein

R is H or $CH_3$,

Y is O or NH, $R_1$ is an alkylene group having from about 2 to about 6 carbon atoms, $R_2$, $R_3$ and $R_4$ are each independently an alkyl group or hydroxyalkyl group having from about 1 to about 22 carbon atoms, and X is a monovalent anion selected from halide and alkyl sulfate having from about 1 to about 4 carbon atoms, or b. diallyldimethylammonium chloride.

64. The personal cleansing composition of claim 63 wherein each conditioner is present in an amount, based upon the total weight of the composition, of from about 0.01 percent to about 0.5 percent.

65. The personal cleansing composition comprising:

a. an carboxyalkyl alkylpolyamine amphoteric surfactant of the formula:

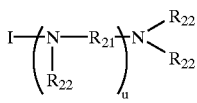

wherein
I is an alkyl or alkenyl group containing from about 8 to about 22 carbon atoms;
$R_{22}$ is a carboxyalkyl group having from about 2 to about 3 carbon atoms;
u is an integer from 1 to 4;
$R_{21}$ is an alkylene group having from about 2 to about 3 carbon atoms and b. an anionic surfactant, c.) optionally a non-ionic surfactant, and d.) at least two conditioners selected from:
1. a cationic cellulose derivative;
2. a cationic guar derivative; and
3. a homopolymer or copolymer of a cationic monomer selected from:
   a. a monomer having the formula

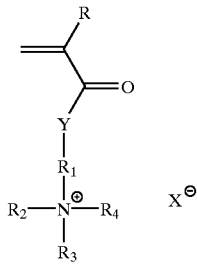

wherein
R is H or $CH_3$,
Y is O or NH,
$R_1$ is an alkylene group having from about 2 to about 6 carbon atoms,
$R_2$, $R_3$ and $R_4$ are each independently an alkyl group or alkyl modified with a hydroxy group having from about 1 to about 22 carbon atoms, and
X is a monovalent anion selected from halide and alkyl sulfate having from about 1 to about 4 carbon atoms, or
   b. diallyldimethylammonium chloride.

66. The personal cleansing composition of claim 65 wherein each of said conditioners are present in an amount, based upon the total weight of the composition, of from about 0.01 percent to about 0.5 percent.

67. A personal cleansing composition comprising:
a. an amidoalkyl sultaine amphoteric surfactant of the formula:

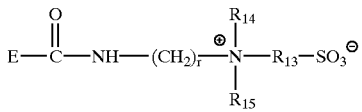

wherein
E is an alkyl group or alkenyl group having from about 7 to about 21 carbon atoms;
$R_{14}$ and $R_{15}$ are each independently an alkyl group or a hydroxyalkyl group having from about 1 to about 4 carbon atoms;

r is an integer from about 2 to about 6; and
$R_{13}$ is an alkylene or hydroxyalkylene group having from about 2 to about 3 carbon atoms;

b. an anionic surfactant, except those anionic surfactants of the group consisting of
1. an alkyl sulfate of the formula

2. an alkyl ether sulfate of the formula

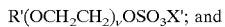

3. an alkylaryl sulfonate of the formula

wherein
R' is an alkyl group having from about 7 to about 14 carbon atoms,
$R'_1$ is an alkyl group having from about 1 to about 12 carbon atoms,
X' is selected from the group consisting of alkali metal ions, alkaline earth metal ions and ammonium ions, and ammonium ions substituted with from about 1 to about 3 substituents; each of the substituents may be the same or different and are selected from the group consisting of alkyl groups having 1 to 4 carbon atoms and hydroxyalkyl groups having from about 2 to about 4 carbon atoms; and
v is an integer from 1 to 5; and c. optionally a non-ionic surfactant, wherein surfactants a through c are present in an amount, based upon the total weight of the personal cleansing composition, of from about 4 percent to about 20 percent.

68. The personal cleansing composition of claim 67 wherein said amphoteric surfactant is cocoamidopropyl hydroxysultaine or mixtures thereof.

69. The personal cleansing composition of claim 67 wherein the anionic surfactant is an alkyl ether sulfosuccinate of the formula:

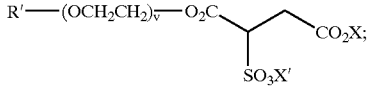

wherein
R' is an alkyl group having from about 7 to about 22 carbon atoms,
X' is selected from the group consisting of alkali metal ions, alkaline earth metal ions, ammonium ions, and ammonium ions substituted with from about 1 to about 3 substituents, each of the substituents may be the same or different and are selected from alkyl groups having from 1 to 4 carbon atoms and hydroxyalkyl groups having from about 2 to about 4 carbon atoms and
v is an integer from 1 to 6
or mixtures thereof.

70. A personal cleansing composition comprising:
a. an carboxyalkyl alkylpolyamine amphoteric surfactant of the formula:

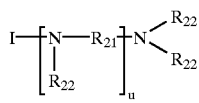

wherein
- I is an alkyl or alkenyl group containing from about 8 to about 22 carbon atoms;
- $R_{22}$ is a carboxyalkyl group having from about 2 to about 3 carbon atoms;
- u is an integer from 1 to 4;
- $R_{21}$ is an alkylene group having from about 2 to about 3 carbon atoms and b. an anionic surfactant, except those anionic surfactants of the group consisting of
  1) an alkyl sulfate of the formula R'—CH$_2$OSO$_3$X'; and 2) an alkylaryl sulfonate of the formula

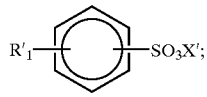

wherein
  - R' is an alkyl group having from about 7 to about 14 carbon atoms,
  - R'$_1$ is an alkyl group having from about 1 to about 12 carbon atoms,
  - X' is selected from the group consisting of alkali metal ions, alkaline earth metal ions and ammonium ions, and ammonium ions substituted with from about 1 to about 3 substituents; each of the substituents may be the same or different and are selected from the group consisting of alkyl groups having 1 to 4 carbon atoms and hydroxyalkyl groups having from about 2 to about 4 carbon atoms; and c.) a non-ionic surfactant selected from polyoxyethylene derivatives of polyol esters, alkyl glucosides, and mixtures thereof;, and d.) a volatile silicone, with the proviso that if the non-ionic surfactant is omitted and the anionic surfactant is an alkyl ether sulfate of the formula R'(OCH$_2$CH$_2$)$_v$OSO$_3$X', then v is greater than or equal to 3.

71. The personal cleansing composition of claim 67 wherein said amphoteric surfactant and said anionic surfactant are present in a weight ratio of from about 3:1 to about 1:3.

72. The personal cleansing composition of claim 67 further comprising at least one conditioner selected from:
  1. a cationic cellulose derivative;
  2. a cationic guar derivative; and
  3. a homopolymer or copolymer of a cationic monomer selected from:
    a. a monomer having the formula

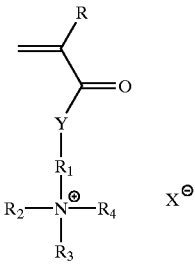

wherein
    - R is H or CH$_3$,
    - Y is O or NH,
    - R$_1$ is an alkylene group having from about 2 to about 6 carbon atoms,
    - R$_2$, R$_3$ and R$_4$ are each independently an alkyl group or hydroxyalkyl group having from about 1 to about 22 carbon atoms, and
    - X is a monovalent anion selected from halide and alkyl sulfate having from about 1 to about 4 carbon atoms, or
    b. diallyldimethylammonium chloride.

73. The personal cleansing composition of claim 72 wherein each conditioner is present in an amount, based upon the total weight of the composition, of from about 0.01 percent to about 0.5 percent.

* * * * *